United States Patent
Christ

(10) Patent No.: US 8,619,134 B2
(45) Date of Patent: Dec. 31, 2013

(54) UNMANNED APPARATUS TRAVERSAL AND INSPECTION SYSTEM

(75) Inventor: Robert D. Christ, Covington, LA (US)

(73) Assignee: SeaTrepid International, LLC, Robert, LA (US)

( * ) Notice: Subject to any disclaimer, the term of this patent is extended or adjusted under 35 U.S.C. 154(b) by 992 days.

(21) Appl. No.: 12/635,493

(22) Filed: Dec. 10, 2009

(65) Prior Publication Data

US 2010/0235018 A1    Sep. 16, 2010

Related U.S. Application Data

(60) Provisional application No. 61/159,315, filed on Mar. 11, 2009, provisional application No. 61/218,799, filed on Jun. 19, 2009.

(51) Int. Cl.
   *H04N 7/18* (2006.01)
(52) U.S. Cl.
   USPC .............................. 348/84; 348/85
(58) Field of Classification Search
   USPC ...................................... 348/82–86
   See application file for complete search history.

(56) References Cited

U.S. PATENT DOCUMENTS

| | | |
|---|---|---|
| 2,427,129 A | 9/1947 | Fields |
| 2,631,315 A | 3/1953 | Hauser |
| 2,657,409 A | 11/1953 | Dawson |
| 3,987,741 A | 10/1976 | Tryon |
| 4,010,619 A | 3/1977 | Hightower et al. |
| 4,030,434 A | 6/1977 | Pedlar et al. |
| 4,034,568 A | 7/1977 | Mason |
| 4,552,594 A | 11/1985 | van Voskuilen et al. |
| 4,620,819 A | 11/1986 | Marsland et al. |
| 4,686,927 A | 8/1987 | Hawkes et al. |
| 4,713,896 A | 12/1987 | Jennens |
| 4,721,055 A | 1/1988 | Pado |
| 5,039,254 A | 8/1991 | Piercy |
| 5,203,646 A | 4/1993 | Landsberger et al. |
| 5,273,376 A | 12/1993 | Ritter, Jr. |
| 5,458,439 A | 10/1995 | Hall et al. |
| 5,593,249 A | 1/1997 | Cox et al. |
| 5,730,551 A | 3/1998 | Skeels et al. |
| 5,770,800 A * | 6/1998 | Jenkins et al. ................. 73/623 |

(Continued)

FOREIGN PATENT DOCUMENTS

| | | |
|---|---|---|
| DE | 930959 | 7/1955 |
| GB | 957180 | 5/1964 |

(Continued)

*Primary Examiner* — Andy Rao
(74) *Attorney, Agent, or Firm* — Baker Donelson, et al.; Warner J. Delaune

(57) ABSTRACT

An unmanned apparatus for use in traversing and inspecting at least a portion of an elongated structure. The unmanned apparatus includes at least one structural member defining a recess sized and configured to receive the portion of the elongated structure. In one aspect, the unmanned apparatus includes a clamping mechanism coupled to the structural member, wherein the clamping mechanism is capable of detachably attaching the unmanned apparatus to the elongated structure. A locomotion system is actuated while the unmanned apparatus is attached to the elongated structure causing the unmanned apparatus to traverse at least a portion of the elongated structure. The unmanned apparatus includes a plurality of cameras and/or at least one sensor capable of providing information regarding the structural integrity of the interior and/or exterior of the elongated structure. A method of inspecting and traversing at least a portion of the elongated structure is also described.

29 Claims, 20 Drawing Sheets

(56) References Cited

U.S. PATENT DOCUMENTS

| | | | |
|---|---|---|---|
| 5,934,832 A | 8/1999 | Baugh |
| 5,975,803 A | 11/1999 | Mackinnon |
| 6,024,514 A | 2/2000 | Östergaard |
| 6,158,370 A | 12/2000 | French et al. |
| 6,223,675 B1 | 5/2001 | Watt et al. |
| 6,234,717 B1 | 5/2001 | Corbetta |
| 6,269,763 B1 | 8/2001 | Woodland |
| 6,276,625 B1 | 8/2001 | Chee et al. |
| 6,290,432 B1 | 9/2001 | Exley et al. |
| 6,312,193 B1 | 11/2001 | Witting et al. |
| 6,371,041 B1 | 4/2002 | Ness |
| 6,390,012 B1 | 5/2002 | Watt et al. |
| 6,439,807 B1 | 8/2002 | Wijsman |
| 6,484,660 B1 | 11/2002 | English |
| 6,512,536 B1 | 1/2003 | Ross |
| 6,600,695 B1 | 7/2003 | Nugent et al. |
| 6,695,539 B2 | 2/2004 | McMillan et al. |
| 6,767,165 B1 | 7/2004 | Corbetta |
| 6,857,486 B2 | 2/2005 | Chitwood et al. |
| 6,928,709 B2 | 8/2005 | McMillan et al. |
| 7,086,807 B2 | 8/2006 | Mackinnon |
| 7,168,387 B1 | 1/2007 | Al-Garni et al. |
| 7,246,567 B2 | 7/2007 | Shelton et al. |
| 7,290,496 B2 | 11/2007 | Asfar et al. |
| 7,296,530 B1 | 11/2007 | Bernstein et al. |
| 7,363,844 B2 | 4/2008 | Barton |
| 7,402,000 B2 | 7/2008 | Bastesen et al. |
| 7,409,919 B2 | 8/2008 | Hoogeveen et al. |
| 7,445,404 B2 | 11/2008 | Giles et al. |
| 7,489,844 B2 | 2/2009 | Shinoski |
| 7,496,002 B2 | 2/2009 | Vosburgh |
| 7,496,226 B2 | 2/2009 | Negahdaripour et al. |
| 8,525,877 B2 * | 9/2013 | Lortie ............... 348/85 |
| 2001/0020435 A1 | 9/2001 | Ghignone |
| 2006/0225771 A1 | 10/2006 | Crawford, III et al. |
| 2007/0258774 A1 | 11/2007 | Thompson et al. |
| 2007/0261629 A1 | 11/2007 | Choi |
| 2007/0269270 A1 | 11/2007 | Bastesen et al. |
| 2007/0276552 A1 | 11/2007 | Rodocker et al. |
| 2007/0283871 A1 | 12/2007 | Millum et al. |
| 2008/0006197 A1 | 1/2008 | Lambertus et al. |
| 2008/0029015 A1 | 2/2008 | Amidon |
| 2008/0041293 A1 | 2/2008 | Diorio et al. |
| 2008/0041294 A1 | 2/2008 | Diorio et al. |
| 2008/0121165 A1 | 5/2008 | Lambertus et al. |
| 2008/0148621 A1 | 6/2008 | Laser |
| 2008/0264323 A1 | 10/2008 | Gosling |
| 2008/0300742 A1 | 12/2008 | Weaver et al. |
| 2008/0302292 A1 | 12/2008 | Ruggaber |
| 2009/0007835 A1 | 1/2009 | Bowen et al. |
| 2009/0050328 A1 | 2/2009 | Bath et al. |

FOREIGN PATENT DOCUMENTS

| | | |
|---|---|---|
| GB | 2027473 A | 2/1980 |
| GB | 2348448 A | 10/2000 |
| JP | 7231528 A | 8/1995 |
| JP | 2007132769 A | 5/2007 |
| WO | WO 8606696 A1 | 11/1986 |
| WO | WO 9003491 A1 | 4/1990 |
| WO | WO 9638688 A1 | 12/1996 |
| WO | WO 9836200 A1 | 8/1998 |
| WO | WO 9839590 A1 | 9/1998 |
| WO | WO 0060262 A1 | 10/2000 |
| WO | WO 0121479 A1 | 3/2001 |
| WO | WO 03036022 A1 | 5/2003 |
| WO | WO 03040602 A1 | 5/2003 |
| WO | WO 03048620 A1 | 6/2003 |
| WO | WO 2004099559 A1 | 11/2004 |
| WO | WO 2004106696 A1 | 12/2004 |
| WO | WO 2005080191 A1 | 9/2005 |
| WO | WO 2006005994 A1 | 1/2006 |
| WO | WO 2006056765 A1 | 6/2006 |
| WO | WO 2008068622 A2 | 6/2008 |

* cited by examiner

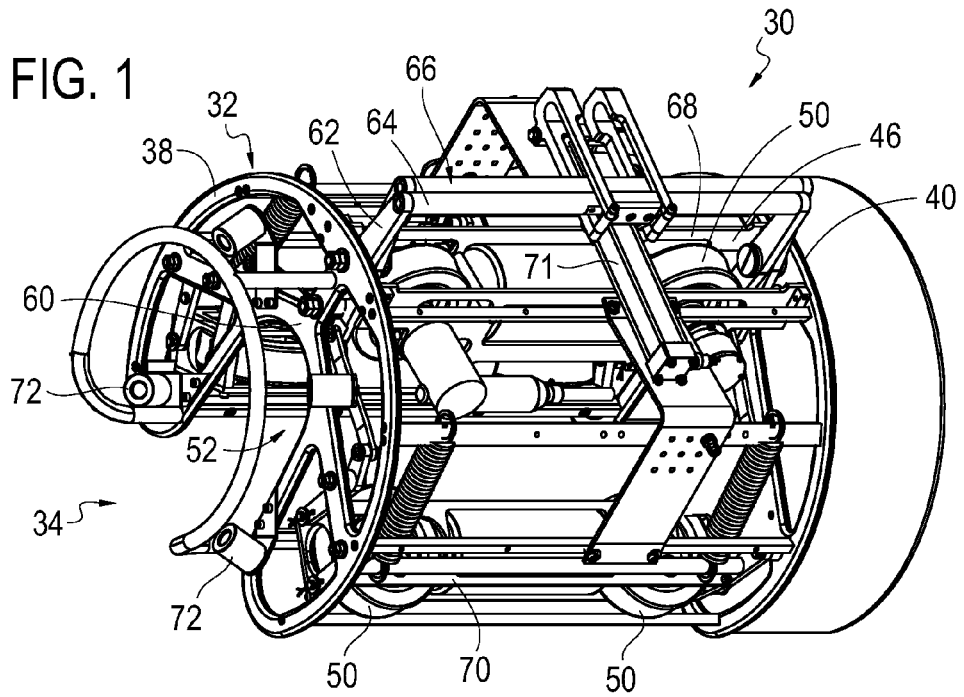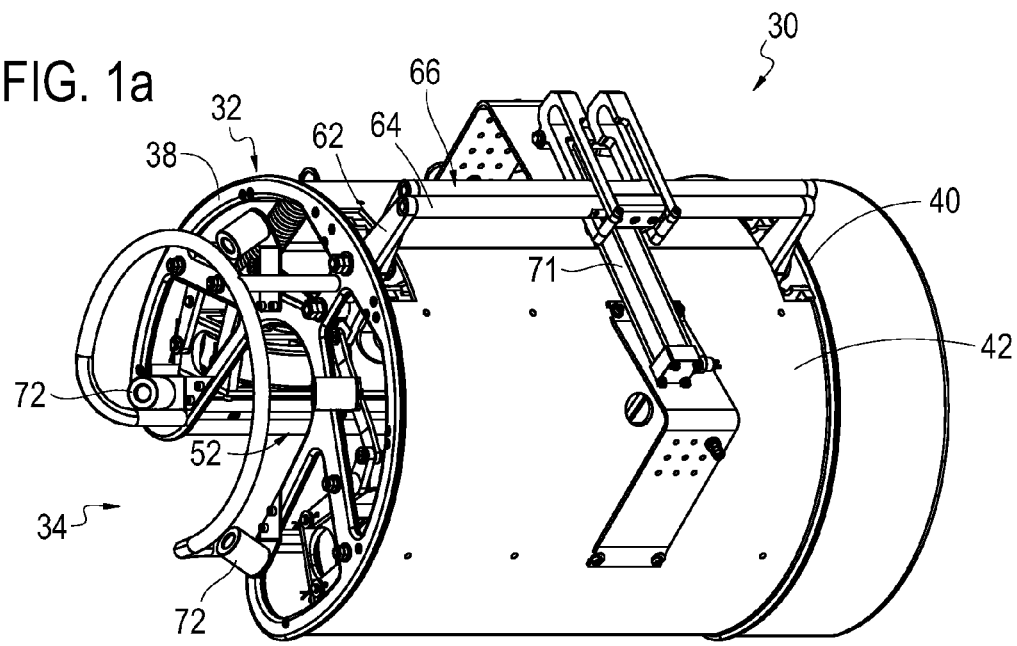

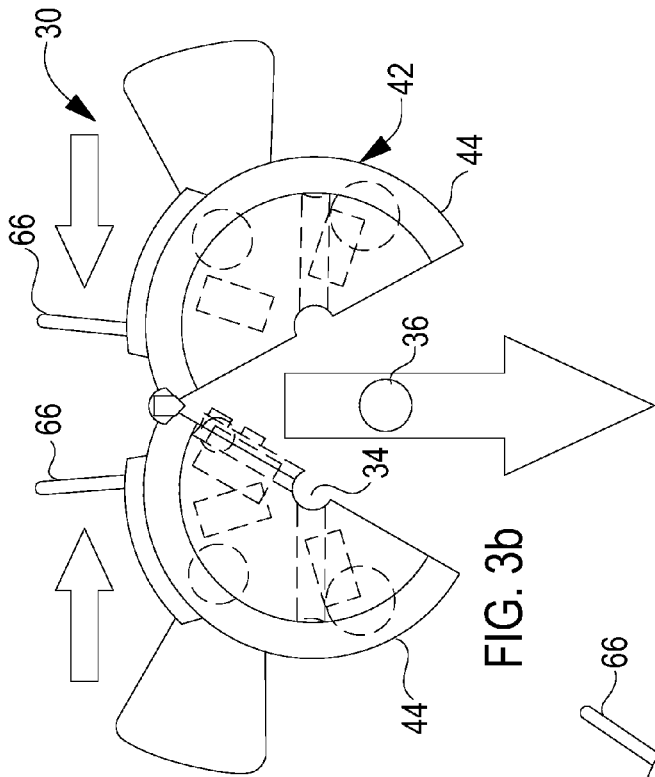
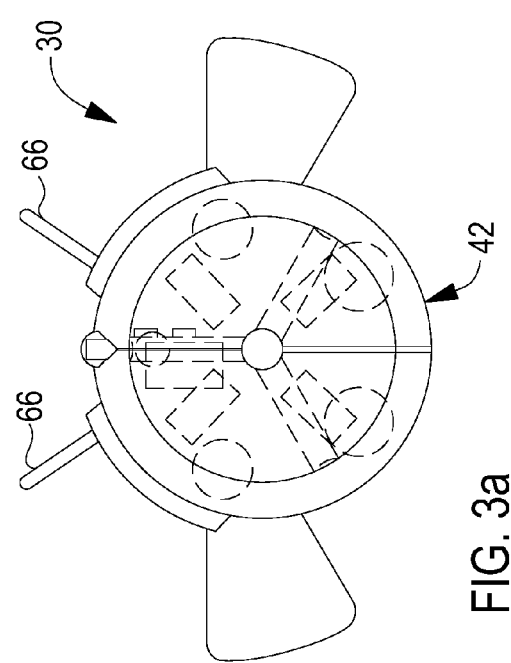
FIG. 3a
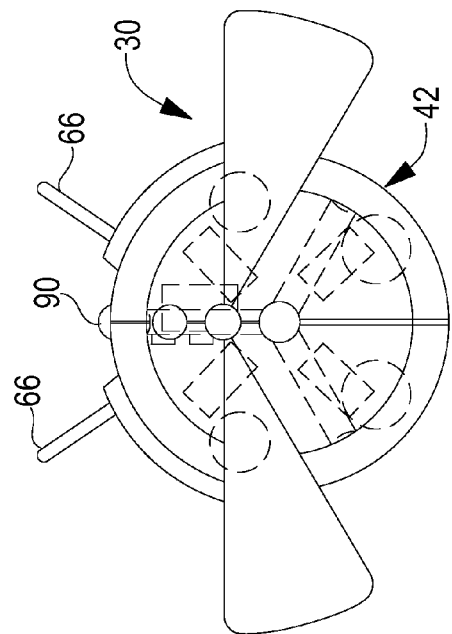
FIG. 4

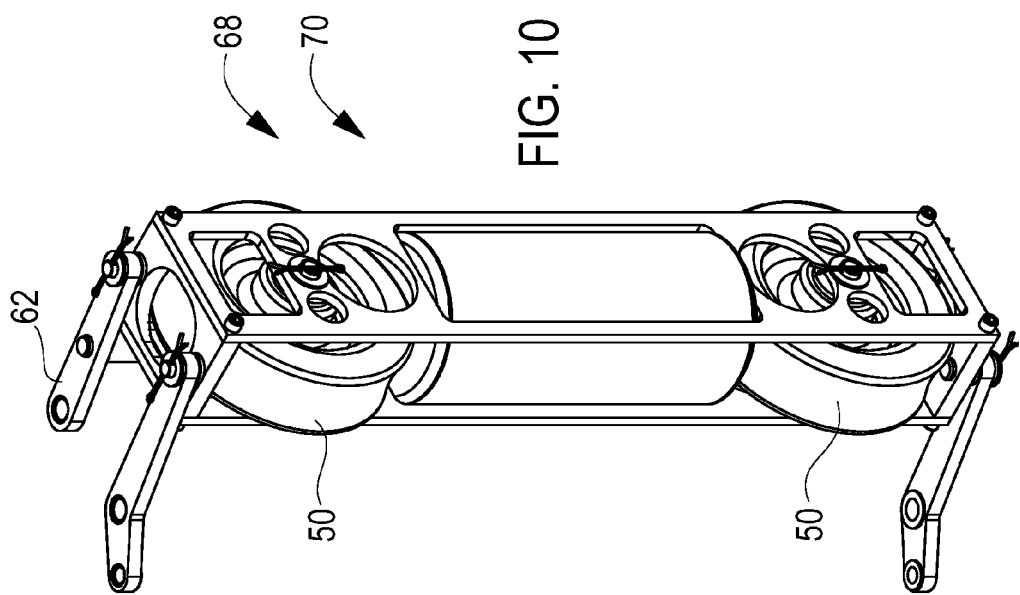
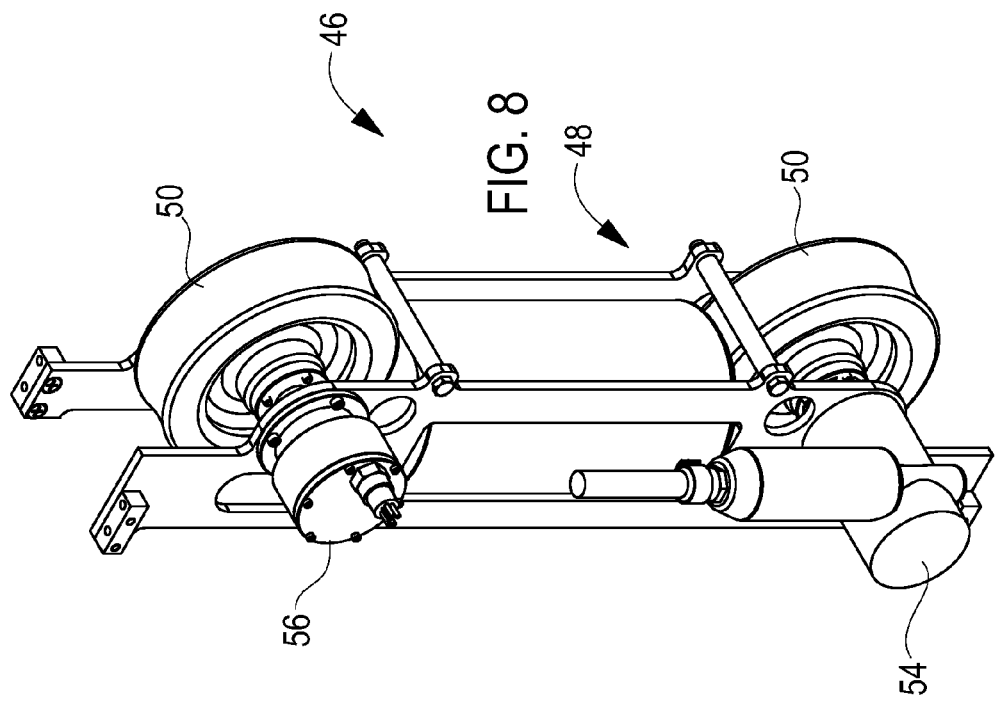

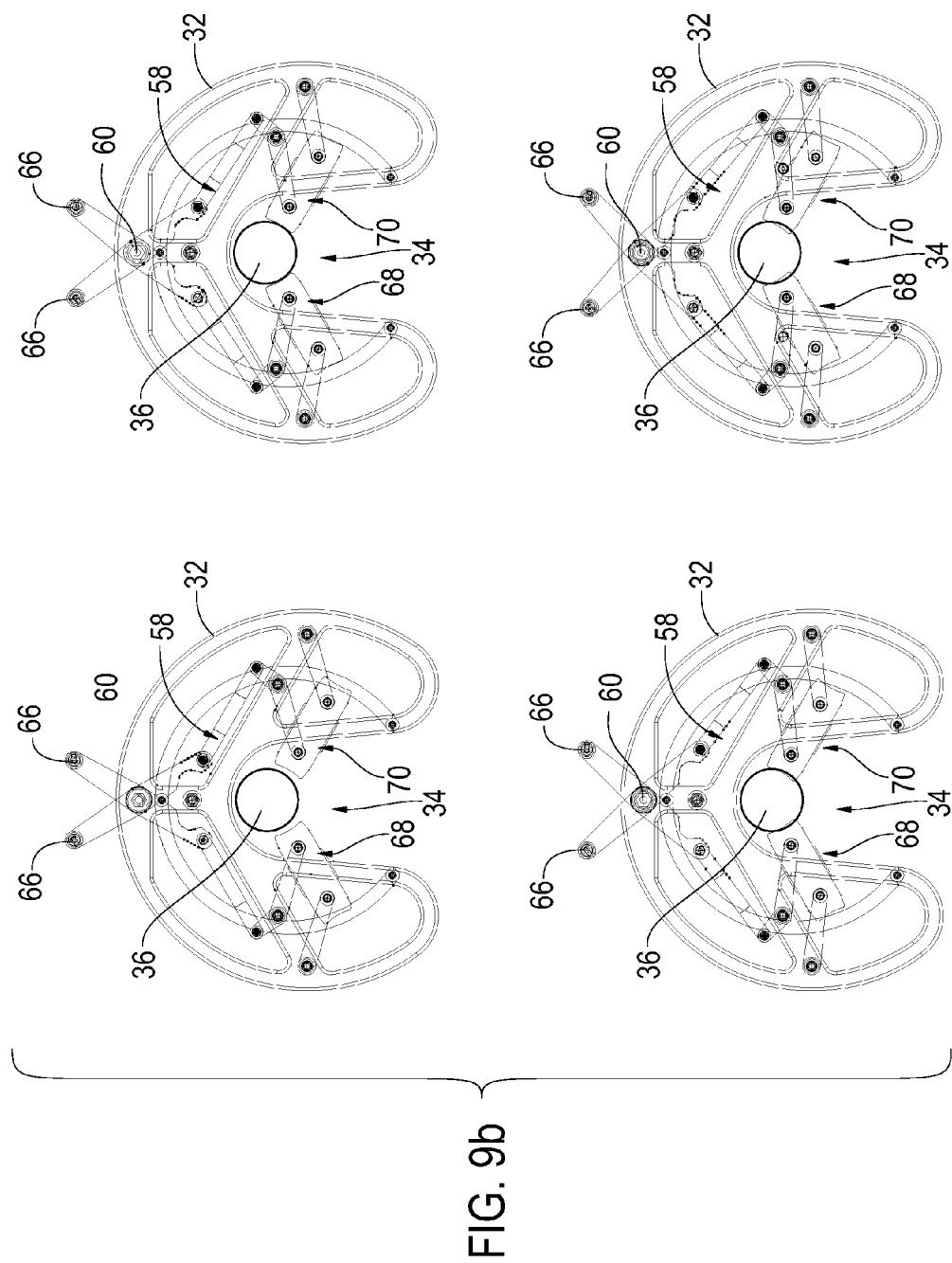

UNMANNED APPARATUS TRAVERSAL AND INSPECTION SYSTEM

REFERENCE TO RELATED APPLICATIONS

A claim is made to the benefit of the priorities of co-owned U.S. Patent Appl. No. 61/218,799, filed on Jun. 19, 2009, and co-owned U.S. Patent Appl. No. 61/159,315, filed on Mar. 11, 2009, the disclosures of which are incorporated herein by reference.

TECHNICAL FIELD

This invention relates to systems and methods of traversing and inspecting structures, specifically, the traversal and inspection of elongated structures using an unmanned apparatus.

SUMMARY OF THE INVENTION

In maritime environments, the inspection of mooring lines, umbilicals, pipelines, jacketed structures and risers is important to determine whether repairs may be needed and to ensure the safety of those working in such environments. Additionally, pipeline monitoring is important during the pipe laying process in order to correctly assess the pipe location and condition at the touchdown point. Typically, divers may be employed to inspect and assess the condition of the pipes, mooring lines, umbilicals, jacketed structures, and/or risers and to determine if further action is necessary. However, in certain circumstances, subsea conditions may be hazardous to the wellbeing of the divers and may unnecessarily place them in dangerous situations. Also, as the depth of drilling in oilfield operations continues to increase, the employment of divers to inspect various subsea items has become more difficult and, in some cases, completely impractical. Additionally, as oilfield operations continue to move into deeper waters, the task of equipment and tool retrieval due to broken lines is becoming more costly and challenging.

In addition to maritime environments, the inspection of pipes, ropes, or lines in certain structures by humans in terrestrial environments may be extremely expensive or time consuming because of the location of the structure. It may also be dangerous to do so in situations wherein the pipes, lines, or ropes are proximate hazardous materials or high voltage. In scenarios where the pipe, line, or rope may be hundreds of feet or more in length, the full inspection of the pipe, rope, or line may be very tedious and cumbersome.

Furthermore, the inspection of pipes, risers, lines, and ropes by humans may be limited usually to a visual inspection of the external surface of the pipe, riser, line, or rope. Typically, there will be no way to determine the internal integrity of the pipe, line, or rope. Although, the pipe, rope, or line may appear to be structurally sound from an inspection of the external surface, there may be serious structural flaws internally. For at least the foregoing reasons, it has become apparent that a need exists for an apparatus and method of traversing and inspecting pipes, lines, ropes, and risers in both maritime and terrestrial environments, wherein an unmanned apparatus is capable of inspecting both the external and internal structural integrity of the pipes, lines, ropes, or risers.

This invention is deemed to address the foregoing need, amongst others, by providing in one of its embodiments an unmanned apparatus capable of traversing a pipe, rope, line, riser, or the like, while inspecting the internal and/or external structural integrity of the traversed structure. Preferably, it will inspect both the internal and external structural integrity of the traversed structure.

Thus, one embodiment of the present invention is an unmanned apparatus for use in traversing and inspecting at least a portion of an elongated structure. The unmanned apparatus comprises at least one structural member defining a recess sized and configured to receive the portion of the elongated structure. The unmanned apparatus further comprises attachment means for attaching the unmanned apparatus to the elongated structure. The attachment means comprises traversal means for traversing at least the portion of the elongated structure. The unmanned apparatus also comprises a plurality of cameras coupled to at least a portion of the unmanned apparatus. The cameras are configured so that the cameras are collectively capable of providing one or more images of the entire surface area of at least the portion of the elongated structure.

Still another embodiment of the present invention is a method of traversing and inspecting at least a portion of an elongated structure using an unmanned apparatus. The method comprises disposing a portion of the elongated structure within a recess defined by a structural member of the unmanned apparatus. The recess is sized and configured to receive the portion of the elongated structure. The unmanned apparatus comprises attachment means for attaching the unmanned apparatus to the elongated structure when the elongated structure is disposed within the recess. The attachment means comprises traversal means for moving the unmanned apparatus relative to at least the portion of the elongated structure. The unmanned apparatus also comprises a plurality of cameras coupled to at least one portion of the unmanned apparatus. The cameras are configured so that the cameras are collectively capable of providing one or more images of the entire surface area of at least the portion of the elongated structure. The method also comprises biasing at least a portion of the traversal means into contact with the portion of the elongated structure and actuating the traversal means so that the unmanned apparatus traverses at least the portion of the elongated structure. The method further comprises capturing with the cameras one or more images of at least the portion of the elongated structure.

Yet another embodiment of the present invention is a method of inspecting the internal structural integrity of at least a portion of an elongated structure. The method comprises coupling a sensor to an unmanned apparatus, wherein the sensor comprises a transmitter proximate a receiver. The method also comprises transmitting at least one wave form having a pre-determined frequency from the transmitter to the elongated structure and receiving the wave form from the elongated structure with the receiver, such that information regarding the internal structural integrity of the elongated structure may be discerned from the received wave form.

Still yet another embodiment of the present invention is an unmanned apparatus for use in traversing and inspecting at least a portion of an elongated structure. The unmanned apparatus comprises at least one structural member. The structural member defines a recess sized and configured to receive the portion of the elongated structure therein. The unmanned apparatus also comprises attachment means for attaching the unmanned apparatus to the elongated structure. The attachment means comprises traversal means for traversing at least the portion of the elongated structure. The unmanned apparatus further comprises at least one sensor coupled to a portion of the unmanned apparatus. The sensor comprises a transmitter proximate a receiver, wherein at least one wave form is transmitted from the transmitter to the elongated structure and thereafter received by the receiver, such that information regarding the elongated structure may be recovered from the wave form.

Another embodiment of the present invention is a method of traversing and inspecting at least a portion of an elongated structure using an unmanned apparatus. The method comprises disposing a portion of the elongated structure within a recess defined by a structural member of the unmanned apparatus. The recess is sized and configured to receive the portion of the elongated structure. The unmanned apparatus comprises attachment means for attaching the unmanned apparatus to the elongated structure when the elongated structure is disposed within the recess. The attachment means comprises traversal means for moving the unmanned apparatus relative to at least the portion of the elongated structure. The unmanned apparatus further comprises at least one sensor comprising a transmitter proximate a receiver, wherein at least one wave form is transmitted from the transmitter to the elongated structure and thereafter received by the receiver, such that information regarding the internal portion of the elongated structure may be recovered from the wave form. The method also comprises biasing at least a portion of the traversal means into contact with the portion of the elongated structure and actuating the traversal means so that the unmanned apparatus traverses at least the portion of the elongated structure. The method further comprises detecting with the sensor information regarding the internal portion of the elongated structure.

These and other features and embodiments of this invention will be still further apparent from the ensuing detailed description and drawings.

BRIEF DESCRIPTION OF THE DRAWINGS

FIG. 1 is a perspective view of an unmanned apparatus consistent with one embodiment of the present invention.

FIG. 1a is a perspective view of an unmanned apparatus comprising a housing consistent with one embodiment of the present invention.

FIG. 2a is a side view of an unmanned apparatus comprising a housing consistent with the embodiment illustrated in FIG. 1a.

FIG. 3a is a front view of an unmanned apparatus comprising a hydrodynamic housing consistent with one embodiment of the present invention.

FIG. 3b is a front view of the unmanned apparatus comprising a hydrodynamic housing wherein the housing comprises separate housing component parts separated to remove an elongated structure from within consistent with the embodiment illustrated in FIG. 3a.

FIG. 4 is a rear view of the unmanned apparatus comprising a hydrodynamic housing consistent with the embodiment illustrated in FIG. 3a.

FIG. 5 is a side view of the unmanned apparatus comprising a hydrodynamic housing detachably attached to an elongated structure consistent with the embodiment illustrated in FIG. 3a.

FIG. 6 is a top plan view of the unmanned apparatus comprising a hydrodynamic housing detachably attached to an elongated structure consistent with the embodiment illustrated in FIG. 3a.

FIG. 7 is a perspective view of the unmanned apparatus comprising a hydrodynamic housing detachably attached to an elongated structure and traversing the elongated structure consistent with the embodiment illustrated in FIG. 3a.

FIG. 8 is a perspective view of a drive unit comprising a hydraulic rotary actuator consistent with one embodiment of the present invention.

FIG. 9b is a front view of the unmanned apparatus comprising attachment means wherein the attachment means comprises a clamping mechanism consistent with the embodiment illustrated in FIG. 1. An elongated structure is disposed within the recess of the unmanned apparatus and the grip bars are moved away from each other to allow clamping mechanism to move the traction members into contact with the elongated structure.

FIG. 10 is a perspective view of an idler unit comprising a plurality of wheels consistent with one embodiment of the present invention.

FIG. 19b is the ROV coupled to the unmanned apparatus with the coupling member, the coupled ROV and unmanned apparatus attached to the elongated structure consistent with the embodiment illustrated in FIG. 19a.

In each of the above figures, like numerals are used to refer to like or functionally like parts among the several figures.

FURTHER DETAILED DESCRIPTION OF THE INVENTION

Illustrative embodiments of the invention are described below as they might be employed in the construction and use of an unmanned maritime or terrestrial crawler traversal and inspection system and method according to the present invention. In the interest of clarity, not all features of an actual implementation are described in this specification. It will be of course appreciated that in the development of such an actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
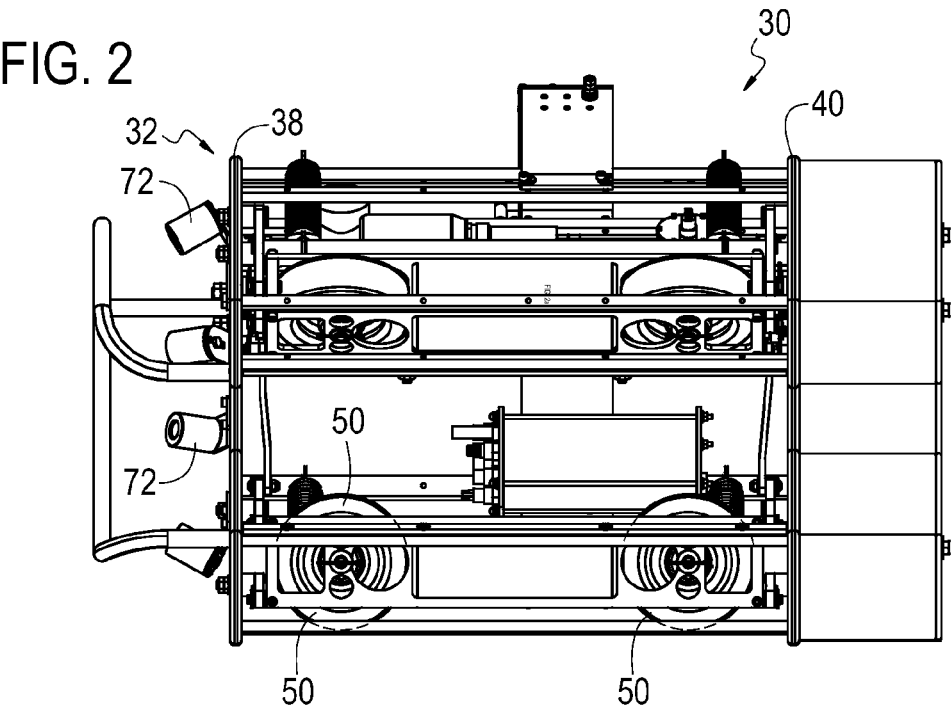
FIG. 2 is a side view of the unmanned apparatus consistent with the embodiment illustrated in FIG. 1.
Figure 2A:
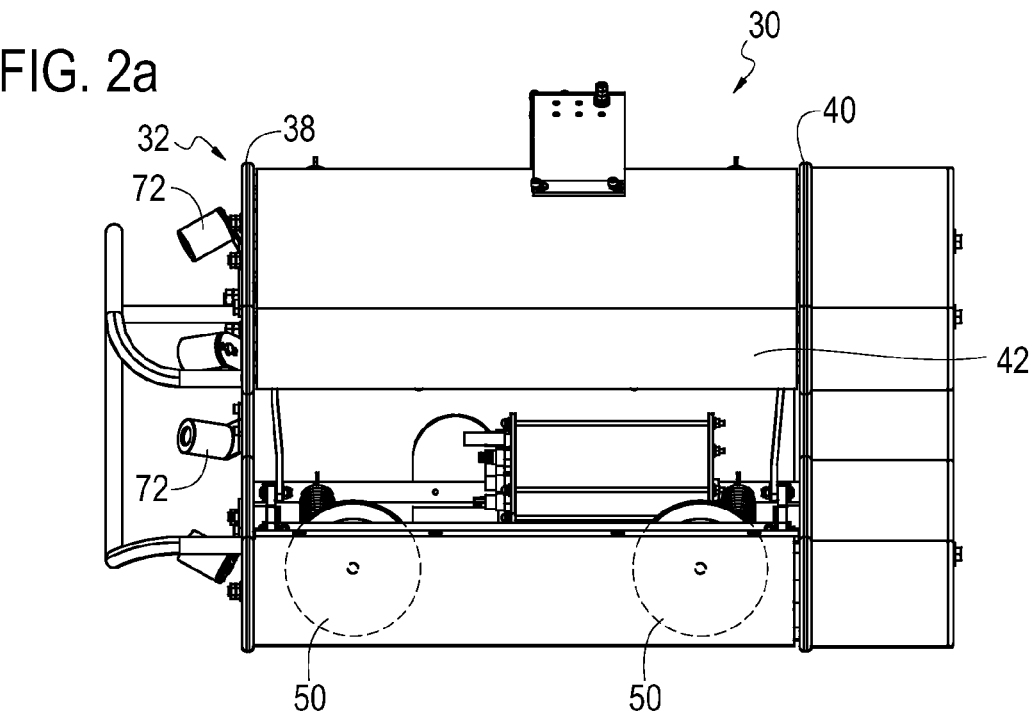
Figure 5:
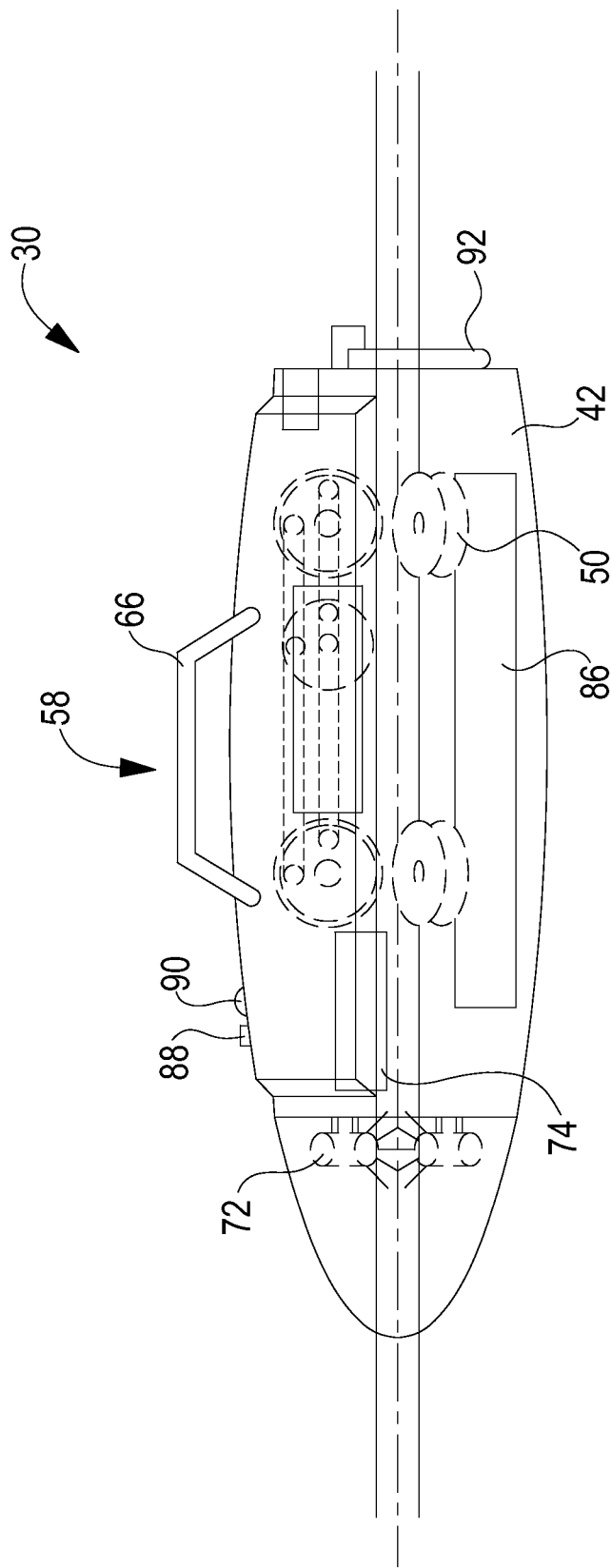
Figure 6:
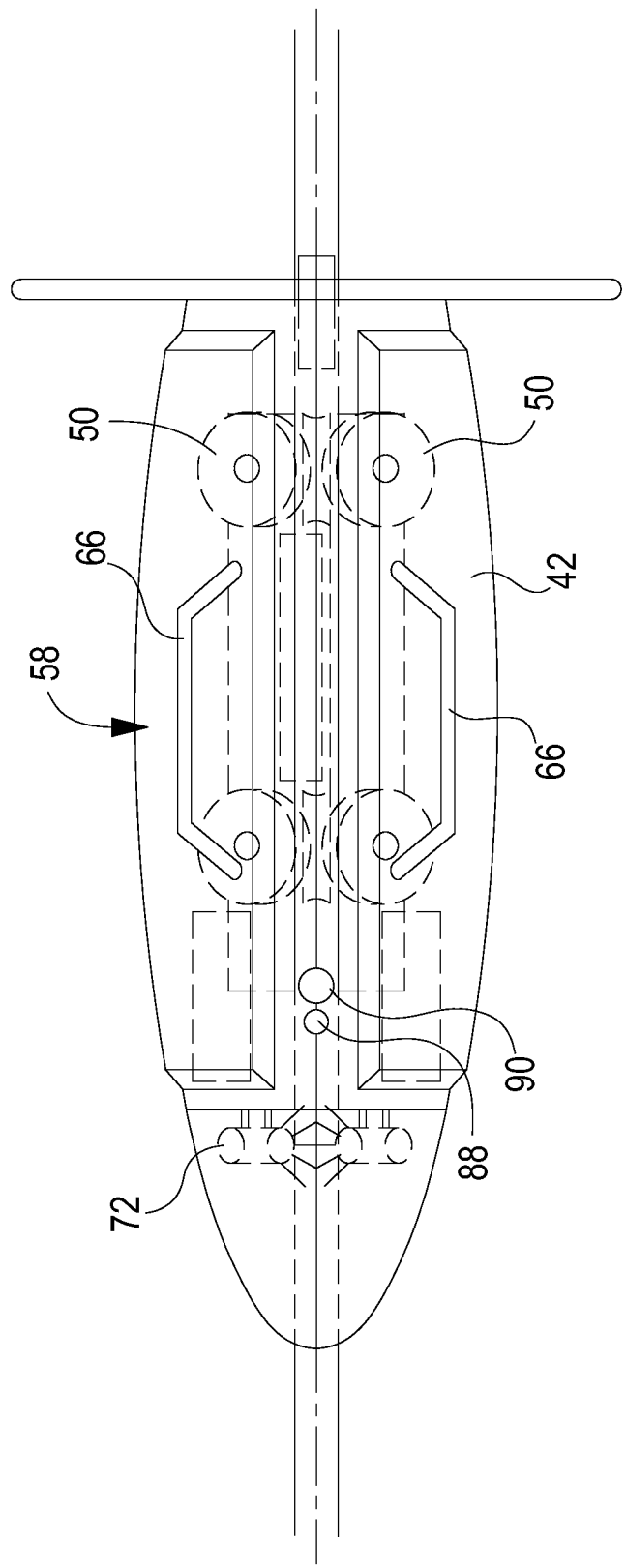
Figure 7:
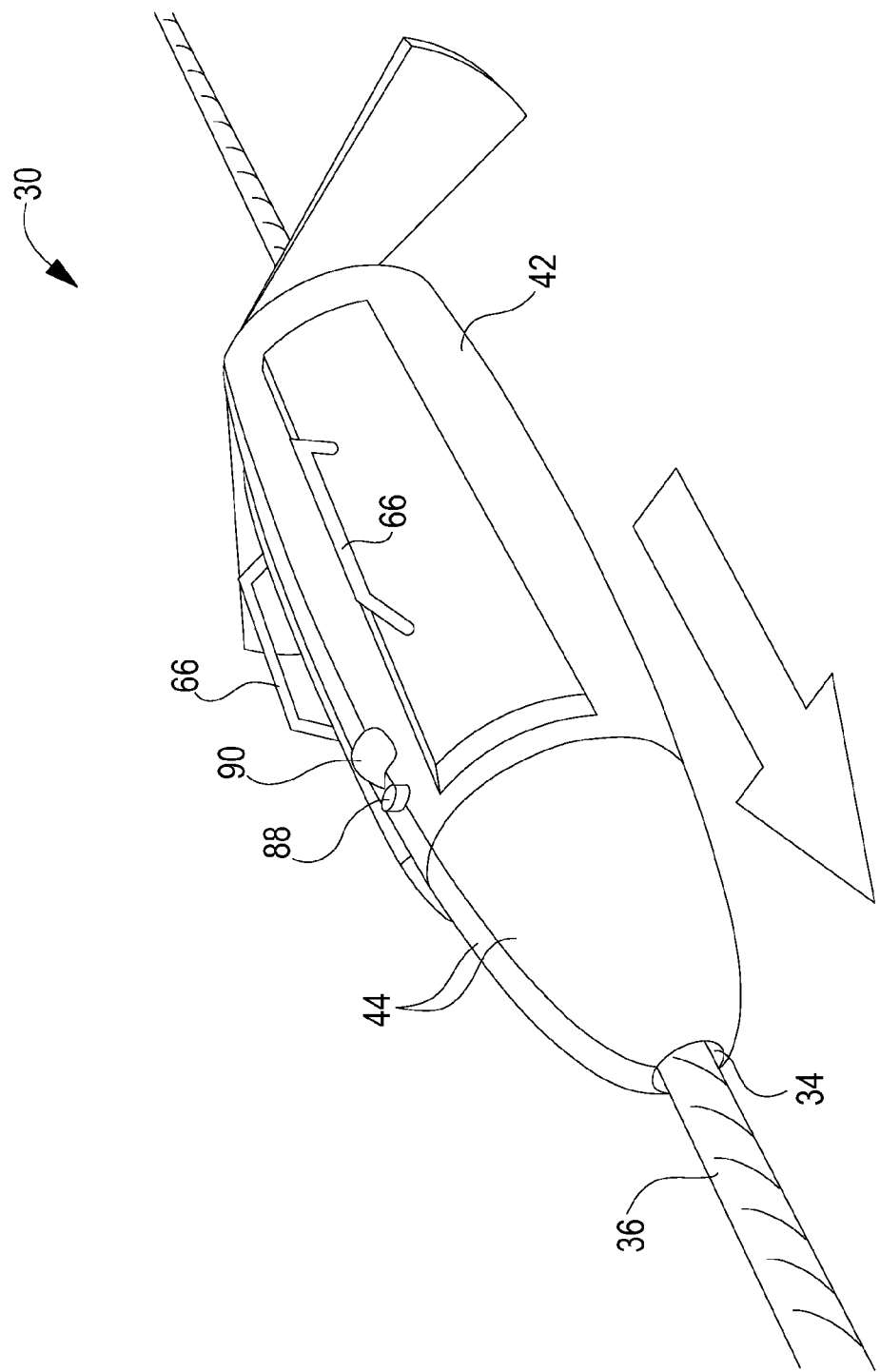

Referring to FIGS. 1 and 2, an illustrative embodiment of an unmanned apparatus constructed in accordance with the principles of the present invention is described. As illustrated, unmanned apparatus 30 is a crawler vehicle comprising a structural member 32 in the form of a frame. Although in this embodiment, the structural member includes the frame of the crawler, it is understood that the structural member may be defined to be one or more of the various components forming the frame, e.g. cross members, structural supports, extension members, and the like. The frame 32 defines a recess 34 sized and configured to receive at least a portion of a structure 36 therein. As mentioned above, typically, the structure traversed will be an elongated structure, such as a pipe, rope, riser, line, or the like. The elongated structure may be a hollow structure or a solid structure. The elongated structure may be made from a variety of materials. Nonlimiting examples include steel, fiber-braided rope, steel rope, metal riser/flow lines, plastic encased metal, synthetic fiber structures, cables and the like. In one embodiment, the elongated structure is a fiber-braided rope, comprising a high-modulus polyethylene material. In another embodiment, the elongated structure is a steel pipe. However, one of ordinary skill in the art will appreciate the crawler of this invention may traverse other structures in need of inspection within the spirit and scope of the present invention. Nonlimiting examples of such other structures may include moorings; marine riser systems, such as petroleum subsea flow lines; and fixed structures, such as jacketed fixed platforms, of underwater or terrestrial moored and/or anchored structures, such as tension leg platforms, moored floating production storage and off-loading platforms, deep-draft caisson vessels, encased umbilical control lines and suspended power lines. As illustrated in FIG. 1 and FIG. 2, the frame 32 comprises a first end portion 38 and a second end portion 40. The recess formed from the frame is generally U-shaped to receive a cylindrical elongated structure; however, the shape and dimension of the recess formed by the frame may vary depending on design choice and the structure(s) for which the crawler will be employed. The frame may consist of multiple cross members and supports to increase structural rigidity and provide mounting points for the clamping mechanism, which will be discussed in detail below. The structure of the frame, including cross members, supports, and mounting points may vary depending on design choice and the shape and size of the crawler and also on the applications for which it will be employed. Such variations may be made while still falling within the scope and spirit of the present invention. As illustrated in an alternate embodiment of FIGS. 1a and 2a, the frame 32 may be at least partially enclosed in a housing 42. In another embodiment, housing may be in the form of a hydrodynamic or aerodynamic shape. In the embodiment shown in FIGS. 3a through 7, a hydrodynamic housing 42 is illustrated wherein the frame 32 is enclosed within the housing to provide more efficient travel through an external medium, in this case, water. The frame 32 in this embodiment is constructed from aluminum; however, the frame may be constructed from other materials. Nonlimiting examples of other suitable materials may include polyoxymethylene plastic commonly known as DELRIN® manufactured by E.I. du Pont de Nemours and Company, abrasion-resistant aluminum, and the like. Housing 42 in the embodiment illustrated in FIGS. 1a and 2a is constructed from polyethylene, although other material could be used depending upon the desired physical properties of the housing and the intended applications. As shown in FIGS. 3a through 7, housing 42 may be sized and configured to further define the recess 34. Housing may be formed from a plurality of housing component parts 44 in order to aid in the disposal of the elongated structure 36 in the recess 34 and removal of the elongated structure from the recess.

Crawler 30 further includes attachment means for attaching the crawler to the elongated structure 36. The attachment means comprises traversal means for traversing at least the portion of the elongated structure 36. In at least one embodiment, the attachment means comprises a plurality of traction members operatively connected to the structural member 32 and the traversal means comprises a locomotion system 48 coupled to at least one of the traction members. The illustrated embodiment of the attachment means and traversal means will now be discussed. As shown in FIGS. 1 and 2, and in more detail in FIG. 8, the crawler 30 has a first traction member 46 coupled to the frame 32. The first traction member, in this embodiment illustrated as a drive unit 46 comprising the traversal means, including a locomotion system 48 and a plurality of wheels 50, is proximate a top portion 52 of the recess 34. The longitudinal axis of the drive unit will be parallel to the longitudinal axis of the elongated structure disposed within the recess. The drive unit contacts the portion of the elongated structure when the portion of the elongated structure is disposed within the recess during use of the crawler. As shown, the drive unit 46 comprises a locomotion system 48, the locomotion system comprising an electric rotary actuator 54 operatively coupled to two wheels 50. The electric rotary actuator used may be any conventional actuator. An example of which is a Model 20WD Rotary Actuator, manufactured by Tecnadyne Company of Rancho Santa Fe, Calif. In an alternate embodiment, a hydraulic rotary actuator may be used. Although the drive unit 46 is shown comprising two wheels 50, any number of wheels may be employed. The locomotion system further comprises an encoder 56 and encoder drive shaft (not shown) operatively coupled to the electric rotary actuator 54 to cause the wheels 50 to turn. It should be appreciated that other traversal means including locomotion systems may be employed. Such other traversal means may include conventional gear and chain assemblies operatively connected to the actuator to cause the wheels to turn, contacting-tracks to rotate, contacting-roller balls to rotate, and the like. Wheels may be constructed from metal or metal alloy, rubber and/or plastic, for example. The surface of the wheel may be concave or compliantly-shaped so as to maximize frictional contact with the structure. In an alternative embodiment, at least one track may be used instead of wheels to provide frictional contact with the elongated structure to allow for traversal along the structure. For example, the crawler may include a tracked drive such as the MINI-TRACS™ manufactured by Inuktun Services Ltd, of Nanaimo, BC, Canada. In another embodiment, ball bearing rollers or castors may be substituted for tracks or wheels so as to mitigate the "Pin-wheeling effect" caused by travel over spiraling rope or pipe.

Figure 9A:
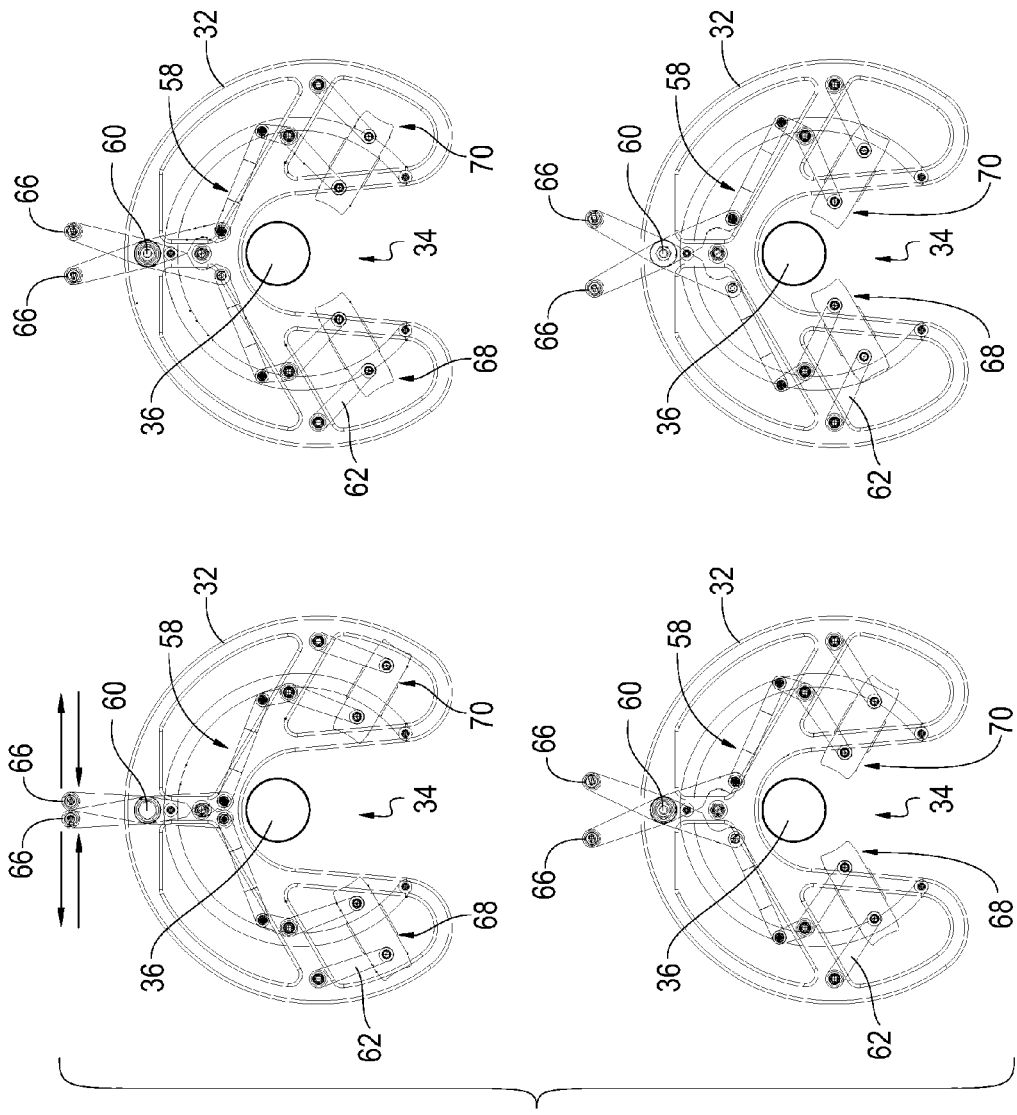
FIG. 9a is a front view of the unmanned apparatus comprising attachment means wherein the attachment means comprises a clamping mechanism consistent with the embodiment illustrated in FIG. 1. An elongated structure is disposed within the recess of the unmanned apparatus and the grip bars have been moved proximate to each other to allow clamping mechanism to separate traction members. The Figure illustrates the movement of the traction members as the grip bars are separated from each other.

In further describing the illustrated attachment means, the crawler 30 further comprises a clamping mechanism 58 as shown in FIGS. 1 and 2, and further illustrated in FIGS. 9a, 9b, and 10. The clamping mechanism 58 comprises at least one hinged member 60 coupled to the structural member 32. In the embodiment illustrated in FIGS. 1 and 2, the clamping mechanism 58 has two hinged members 60 formed from the junction of a plurality of elongate members 62, illustrated as flattened bars, attached to the frame 32. The flattened bars 62 form the support structure of the clamping mechanism and enable the various components of the clamping mechanism to interact and function as intended. As shown at least in FIGS. 1 and 1a, two flattened bars 62 extend from and above each end portion 38,40 of the crawler 30 wherein each flattened bar of each end portion is connected to its respective flattened bar of the other end portion by an elongated bar 64, thus forming a pair of grip bars 66 extending from the crawler. The longitudinal axis of each grip bar is parallel to the longitudinal axis of the crawler. The clamping mechanism 58 further comprises a second traction member 68 operatively coupled to the hinged member 60 by a plurality of flattened bars 62 and a third traction member 70 operatively coupled to the hinged member by a plurality of flattened bars. As illustrated, the second and third traction members are passive idler units 68,70 comprising two wheels 50 wherein there is no actuator or motor operatively connected to the wheels. The wheels provide for frictional contact with the elongated structure so that the crawler may traverse the elongated structure. The idler units may comprise respective tracks in place of the wheels. Other frictional based traversal methods may be used. One such nonlimiting example may be castors. Although it is illustrated as the drive unit 46 located at the top portion of the recess 34, the drive unit may be employed in place of the second 68 and/or third traction system 70 or all three traction systems may be drive units. In at least one embodiment, the first traction member, second traction member, and third traction member are substantially equidistant from each other when the first traction member, the second traction member, and the third traction member contact the portion of the elongated structure.

As illustrated in FIGS. 1 and 2, the grip bars 66 and idler units 68,70 are interconnected through the flattened bars 62 and the junction of the flattened bars attached to the frame 32 forms a hinge member 60 at each end portion 38,40 of the crawler. A plurality of springs (not shown) are also mounted on the crawler 30 and bias the clamping mechanism 58 in a closed position whereby the idler units 68,70 default to a location within the recess 34 and in contact with the elongated structure 36 if disposed within the recess. The clamping mechanism 58 in operation is illustrated in FIGS. 9a and 9b. As shown, the clamping mechanism 58 is sized and configured so that the clamping mechanism may be selectively biased to contact or separate from the elongated structure 36 based on the intended use of the crawler 30. The second and third traction systems 68,70, illustrated as idler units, are brought into contact by the movement of the grip bars 66. In at least one embodiment, a linear actuator 71 is operatively connected to the grip bars, wherein the linear actuator provides the force moving the grip bars inward, thus increasing the distance between the idler units allowing for the elongated structure to be disposed within the recess. The force is then removed from the grip bars by the linear actuator and the idler units move inward toward the elongated structure due to the spring loaded bias until the wheels of the idler units contact the elongated structure. To traverse the elongated structure, the locomotion system is actuated while the drive unit and the idler units contact the elongated structure. The drive unit and idler units thereby cause the unmanned apparatus to traverse and inspect at least a portion of a length of the elongated structure.

Alternate attachment means may include mechanical separation and spring-loaded attachment of the clamping mechanism with a manipulator member or a "fail to close" trapping mechanism, similar to the operation of a simple household mousetrap, to easily install the vehicle upon the elongated structure.

Illustrated in FIGS. 1 and 2, a plurality of cameras 72 are coupled to at least a portion of the crawler 30. In the illustrated embodiment, the cameras 72 are coupled to one end portion 38,40 of the frame. The cameras are configured so that the cameras provide one or more images of the entire surface area of at least the portion of the elongated structure. This may be accomplished by mounting cameras around the perimeter of the end portion 38,40 as illustrated in FIG. 1 to provide an overlapping field of view of the elongated structure. The cameras may be conventional commercial cameras, such as a CRYSTAL CAM®, manufactured by Inuktun Services, Ltd. of Nanaimo, BC, Canada. The cameras may allow for pixel counting, enabling the external structure and the measured outer diameter of the elongated structure to be analyzed. The cameras are typically mounted on the end portion of the crawler traversing in the direction of the area inspected. This end portion is typically the end portion proximate the water surface. In an alternate embodiment, at least one camera is mounted on the end portion opposing the inspected portion of the elongated structure, typically the end portion facing the sea floor, whereby the camera captures a macro view of the mooring/riser and surrounding environment on the sea floor-facing end of the crawler.

In an alternate embodiment, the crawler comprises at least one sensor 74 coupled to at least one of the following: (i) the structural member 32; (ii) the first traction member 46; (iii) the second traction member 68; (iv) the third traction member 70; (v) the housing 42; (vi) a thruster 76; and/or (vii) the locomotion system 48. Each sensor detects at least one parameter indicative of the elongated structure, the external environment, and/or the crawler. Such sensors may incorporate sound velocity profiling, acoustic attenuation measurement and internal radiographic imaging of the internal structure of the rope for characterizing the rope structure. In at least one embodiment, the sensor 74 comprises a transmitter 78 proximate a receiver 80. At least one wave form having a pre-determined frequency is transmitted from the transmitter to the elongated structure. The wave form is received from the elongated structure with the receiver, such that information regarding the internal structural integrity of the elongated structure may be discerned from the received wave form. In one embodiment, the sensor generates a wave form having a pre-determined frequency of at least about twenty kilohertz. In one embodiment, the operator may vary the pre-determined frequency selected; however, it is preferable that the frequency remain in the ultrasonic range. The pre-determined frequency may be generated by the sensor or by an external wave form generator 82. The wave form generator may be any conventional wave form generator capable of producing frequencies in the ultrasonic and/or x-ray frequency range. In one embodiment, the sensor transmits an ultrasonic wave from the transmitter to the elongated structure 36. The receiver 80 receives the reflected wave form from the elongated structure 36. Characteristics of the received wave form, such as the intensity of the received wave form and the time interval between transmission and reception of the wave form may allow information regarding the internal structural integrity of the elongated structure to be determined. The transmitter, receiver, and signal generator may be housed in one device, typically referred to as a transducer 84.

In an alternate embodiment, the transmitter 78 and receiver 80 may be coaxial and located on opposing sides of the elongated structure 36. The transmitter transmits the generated wave form having a pre-determined frequency to the elongated structure. The receiver on the opposing side of the transmitter receives the wave form. Information regarding the elongated structure may be determined by measuring, for example, the velocity of the wave form transmitted and/or the magnitude of the received wave form. In one embodiment, the wave form has a pre-determined frequency of at least about twenty kilohertz. The operator may vary the pre-determined frequency selected; however, it is preferable that the frequency remain in the ultrasonic range. In an alternate embodiment, the wave form has a pre-determined frequency of at least about 30 petahertz. The operator may vary the pre-determined frequency selected; however, it is preferable that the frequency remain in the x-ray range. In embodiments employing radio frequency, specifically x-ray frequency, the receiver will be any detector or image receptor appreciated by those of ordinary skill in the art.

In an alternate embodiment, the crawler will include at least one of the following sensors: a three-axis gyrometer, magnetometer, and/or accelerometer for sensing crawler orientation. Such components may be conventional components such as the TCM suite of products manufactured by Precision Navigation, Inc. of Santa Rosa, Calif. or the 3DM-GX1® Attitude Heading Reference System (AHRS) manufactured by MicroStrain, Inc. of Williston, Vt. for orientation and the Fiber Optic Gyrometer manufactured by CDL of Aberdeen, Scotland. Alternate embodiments may also include a pressure-sensing depth gauge, such as the DIGIQUARTZ® Pressure Sensitive Depth Transducer manufactured by Paroscientific, Inc. of Redmond, Wash.

In one embodiment, the crawler includes a conventional linear contact or non-contact distance encoder 56 for measuring distance traveled along surface of structure, such as the MES-20-100P, manufactured by Microtech Laboratory, Inc. of Kanagawa, Japan.

In one embodiment, the crawler includes a conventional mechanical or infrared "Bump" sensor for direction change at the end of the elongated structure when in untethered mode, such as the Roomba 500 bumper switches and cliff sensors, manufactured by iRobot Corporation of Bedford, Mass.

High-density digital capture of sensor data within the crawler's electronic components may be accomplished by a conventional storage device such as the X-25M solid-state drive manufactured by Intel Corporation of Santa Clara, Calif. In an alternate embodiment, the data may be stored remotely from the vehicle, wherein the drive may be located at the control console, discussed below, with data link via optical fiber or copper serial or Ethernet transmittal. Easy access may be granted to the video and data capture card via an electronics component mechanical quick disconnect as well as a conventional wet-mateable underwater connector, such as the Micro WET-CON family of connectors manufactured by SEA CON® Brantner and Associates, Inc. of El Cajon, Calif., for direct electrical/data connection to the storage card for data download/program upload, thus avoiding having to open the sealed electronics components.

In one embodiment, batteries 86 for locomotion, manipulation and control in an untethered model include conventional battery components, such as the lead-Acid, Ni-cd, Ni-MH, or Li-ion battery, manufactured by Kokam America Inc. of Lee's Summit, Mo. Batteries may be charged in a housing with the housing easily detachable from vehicle when in the untethered model. In an alternate embodiment, a strobe light 88 for recovery at surface may use conventional battery components, such as the ST3K Xenon Rechargeable Submersible Strobe, manufactured by Bowtech Products Ltd of Aberdeen, Scotland.

In one embodiment, the crawler may be tracked and communicated acoustically with a conventional acoustic positioning and/or data communications system 90, such as the Sonardyne International Ltd of Hampshire, UK or Kongsberg Maritime of Kongsberg, Norway acoustic positioning and acoustic modem products. Acoustic Positioning System with modem may also be used for crawler location and remote communication, such as the Sonardyne or Kongsberg Maritime acoustic positioning and acoustic modem products.

In one embodiment, the crawler may be positively uncoupled from the elongated structure should power or communications with the crawler be lost via physical tether-strain on the vehicle's spring-loaded attachment system or via a springload-to-open fail mechanism. This may be accomplished by an activated remote acoustic release via conventional acoustic modem such as the Telesonar Suite of products, manufactured by Benthos Inc. of North Falmouth, Mass., as well as a manual manipulator "squeeze" release by an external force on the grip bars by a manipulator member which will be discussed further below.

In at least one embodiment, sacrificial deployment weights 92 made from concrete or other environmentally-friendly substance may be used for buoyancy control in the untethered mode. These sacrificial deployment weights may be hung externally from the vehicle for ease of discharge and may be shed at the bottom via withdrawal of a retaining rod, where in the rod is actuated via a conventional electrical linear actuator such as the Model 218 Linear Actuator, manufactured by Tecnadyne Company of Rancho Santa Fe, Calif.

In one embodiment, the crawler includes conventional syntactic foam buoyancy, such as the AUV buoyancy solutions, manufactured by Floatation Technologies, Inc. of Biddeford, Me., rated to the depth of the specific subsea operation, to counteract the vehicle's negative weight in water, which is the overall positive buoyancy before addition of sacrificial deployment weights in subsea operations.

Inspection of the elongated structure will be completed by the operator or one skilled in the art after the information gathered from the crawler and/or ROV is transmitted and/or received from the crawler at the surface control station further discussed below. Although the crawler may not interpret the information gathered from the sensors, the crawler is an integral part of the inspection process as it is responsible for the collection of much of the information required to inspect the elongated structure. Alternatively, the crawler may include a processor component capable of providing one or more conclusions regarding the integrity of the elongated structure based on the information gathered by the sensors.

In one embodiment, the crawler 30 is used in a system to traverse and inspect at least a portion of an elongated water structure. The system further comprises a remotely operated vehicle (ROV) 94. In one embodiment, the ROV 94 provides a coupling member wherein the coupling member is sized and configured to couple the ROV to the crawler. A surface control station 96 located on a vessel 98 or moored structure 100 will be controlled by an operator, the operator relaying instructions to the ROV through a primary cable 102 coupling the surface control station to the ROV. The surface control station may be a command center located in the vessel configured to relay instructions to the ROV. The primary cable may be a coaxial cable capable of transmitting information and/or energy between the ROV and the surface control station. In an alternate embodiment, the primary cable may be a twisted pair electrical conductor and/or an optical fiber wherein the twisted pair electrical conductor may transmit energy and/or information between the surface control station and the ROV and the optical fiber may transmit information between the surface control station and ROV. As stated below, the crawler may be operated in a tethered or untethered mode. In the tethered mode, crawler may be coupled to the ROV by a coupling member and by a secondary cable 104, wherein the secondary cable may be a coaxial cable wherein energy and information are transmitted between the crawler and ROV. In an alternate embodiment, secondary cable may be a twisted pair electrical conductor and/or optical fiber, wherein the twisted pair electrical conductor may transmit energy and/or information between the crawler and the ROV and the optical fiber may transmit information between the crawler and ROV. In an alternate embodiment wherein the crawler is in tethered mode, crawler may be coupled to the surface control station by a tertiary cable 106. The tertiary cable may be a coaxial cable wherein energy and information are transmitted between the crawler and the surface control station. In an alternate embodiment, tertiary cable may be a twisted pair electrical conductor and/or optical fiber, wherein the twisted pair electrical conductor may transmit energy and/or information between the crawler and the surface control station and the optical fiber may transmit information between the crawler and surface control station.

The crawler may be operated in a tethered or untethered mode. In one embodiment, the crawler 30 is operated in an untethered mode as shown in FIGS. 12 through 18. Operators aboard a vessel of opportunity 98 or aboard a moored structure 100 attach one or more crawlers to a launch assembly 108, illustrated as a deployment and retrieval line or rope, and hang it over the side of the boat for easy access via a Remotely Operated Vehicle (ROV) 94. The crawler may be attached to the line by any conventional method known to one of ordinary skill in the art. Such nonlimiting methods of attachment include a receptacle attachment to the deployment line, a caged deployment garage, a line similar to the elongated structure being inspected including a mechanical stop, e.g., large washer with a knot to counter slippage. The crawler vehicle may be placed on a deployment rope in series for multiple simultaneous placements of crawlers on multiple moorings/risers. The deployment rope, illustrated with multiple vehicles attached, is hung over the side, below keel level, for easy access by the ROV.

Figure 11:
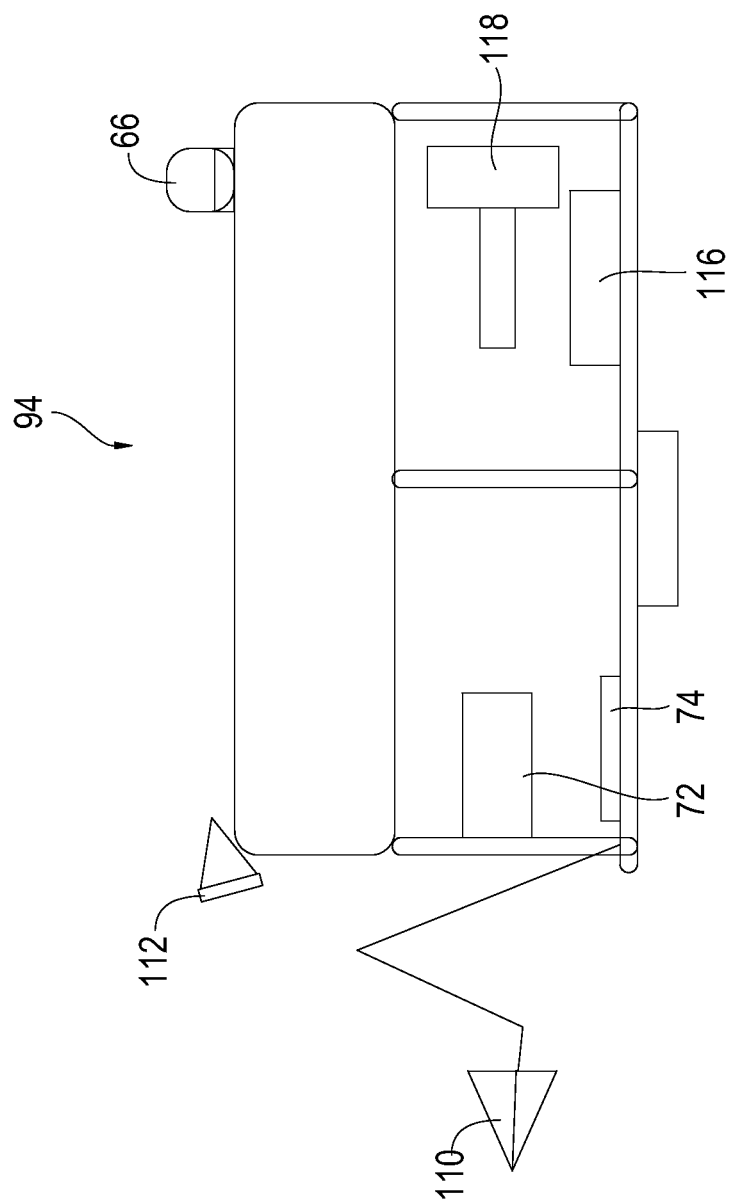
FIG. 11 is a remotely operated vehicle (ROV) consistent with one embodiment of the present invention.
Figure 12:
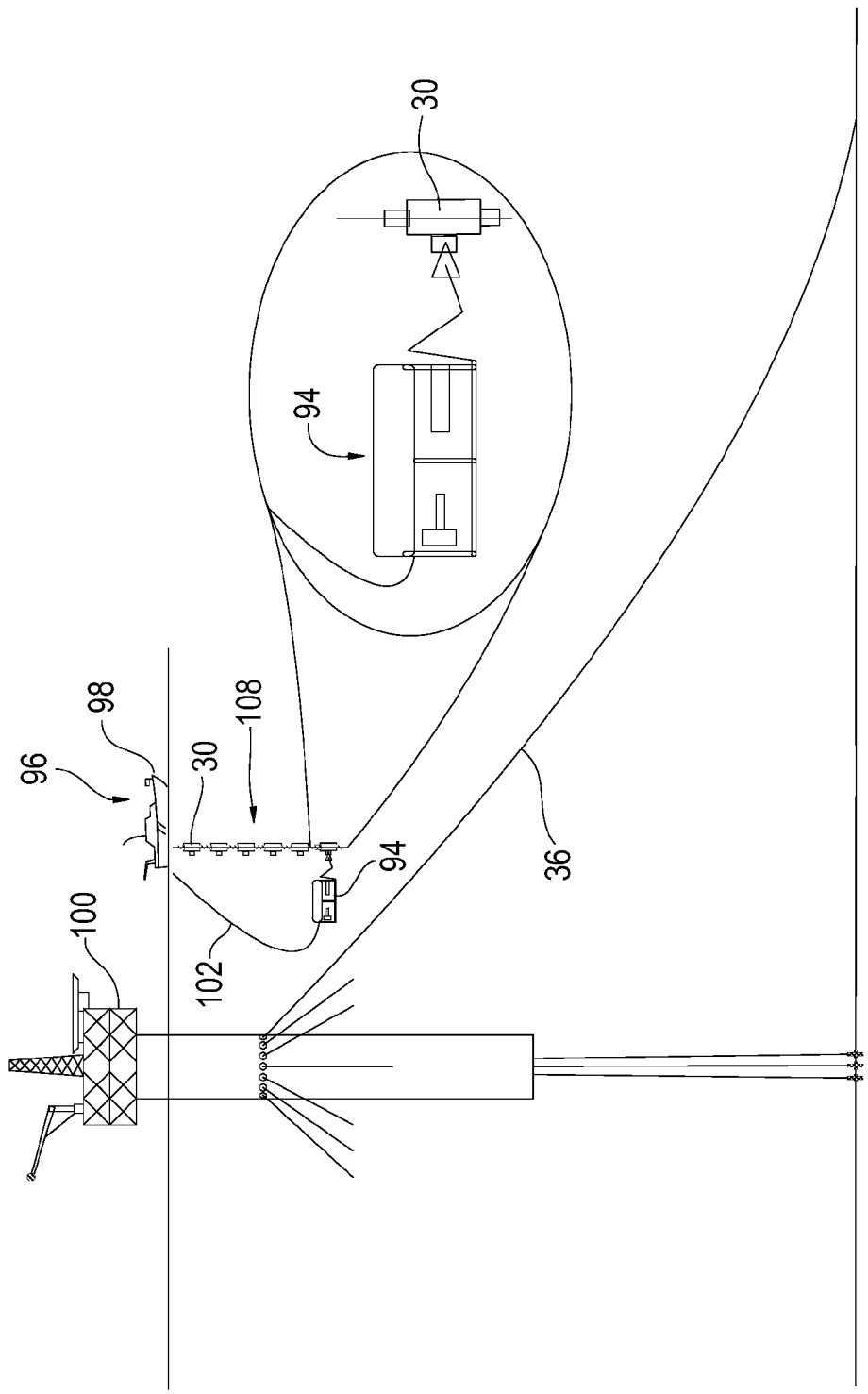
FIG. 12 is a perspective view of a ROV comprising a manipulator member detaching an unmanned apparatus from a launch assembly consistent with one embodiment of the present invention.

The ROV 94 shown in FIG. 11, and further illustrated in FIG. 12, may be any commercial version, but will preferably be a large observation class ROV in the vehicle size range of 2,000 pounds (900 kg). One such commercial version is the MaxRover ROV, manufactured by Deep Sea Systems International, Inc. of Falmouth, Mass. In at least one embodiment, the ROV is equipped with a coupling member, illustrated as a multi-function manipulator member 110, sufficient to place the crawler upon the line. One such nonlimiting example of a manipulator member is the Electro-hydraulic 5-function manipulator manufactured by Hydro-lek Ltd. of Berkshire, UK. The manipulator is sized and configured to attach and detach the crawler from the line(s) to be inspected. The ROV may also have at least one video camera 72 and/or variable intensity lights 112. A float block and weights 92 may be detachable attached to the ROV to provide vertical stability. The coupling member may be a manipulator member 110 used to detach and attach the crawler to and from the deployment rope and also the elongated structure. Coupling member may also include a coupler 114, in the form of a connecting brace discussed further below, used to couple the ROV to the crawler 30 while inspecting the rope 36. The coupler 114 may also allow for the ROV and the crawler to form an integral unit.

Figure 19B:
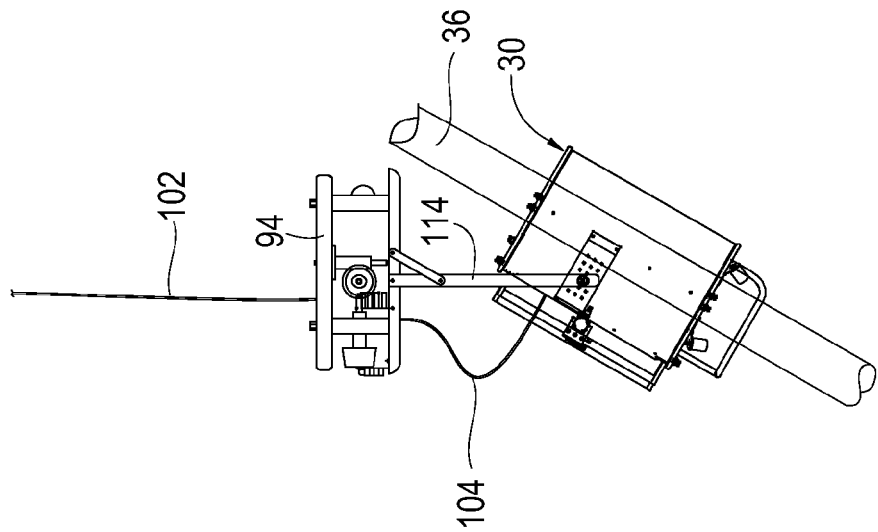
Figure 19A:
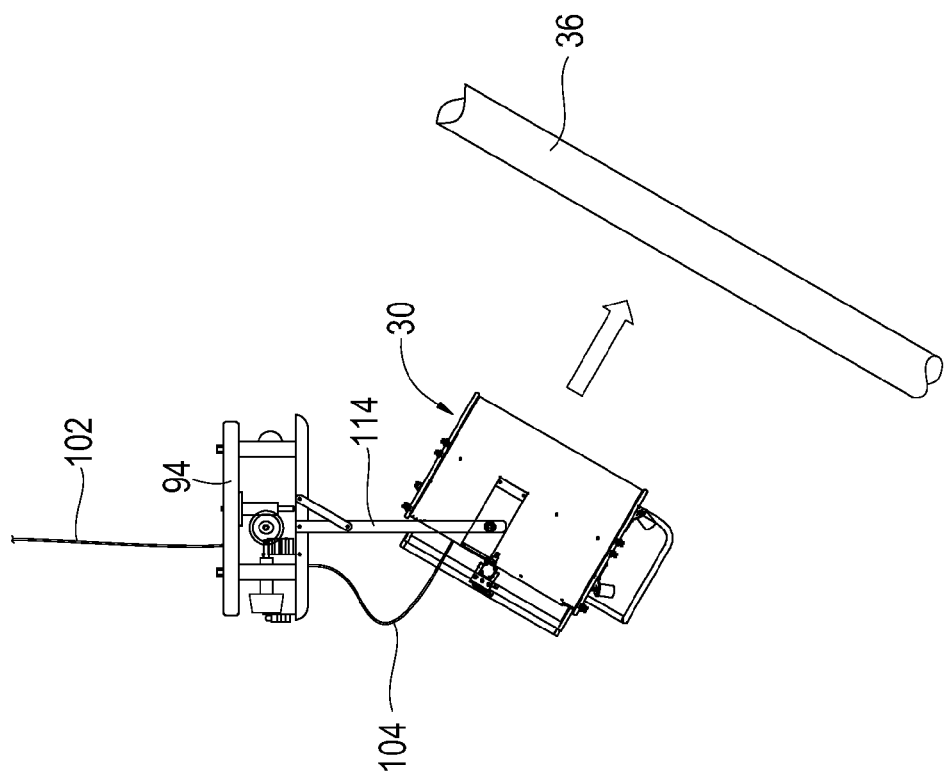
FIG. 19a is a ROV coupled to an unmanned apparatus with a coupling member, the coupled ROV and unmanned apparatus propelled by at least one thruster toward an elongated structure consistent with one embodiment of the present invention.

The ROV 94 may be tethered to the crawler 30. In at least one embodiment, the tether is a secondary cable 104, illustrated in FIGS. 19a and 19b as a coaxial electrical conductor, wherein energy and information are transmitted. The tether may transmit information from the sensors 74 to the ROV. The ROV may also transmit information and/or energy to the crawler, including energy sufficient to recharge the batteries of the crawler. In alternate embodiments, the tether may be a twisted pair electrical conductor and/or optical fiber wherein the twisted pair electrical conductor may transmit energy and/or information between the crawler and the ROV and the optical fiber may transmit information between the crawler and ROV. The ROV may include a power conversion system to develop working voltages from the high voltage present on the tether.

In at least one embodiment, the ROV 94 includes a navigation package which may include a depth sensor, a magnetometer, and an inertial measurement unit. Additionally, the ROV may include an acoustic locator beacon/modem to track the vehicle. The components discussed above may be enclosed in an electronics housing(s) 116. The ROV may have thrusters 118 to provide locomotion for the ROV once submerged. In at least one embodiment, the crawler may contain at least one thruster to aid in propulsion and navigation in either the tethered or untethered operation mode.

Figure 13:
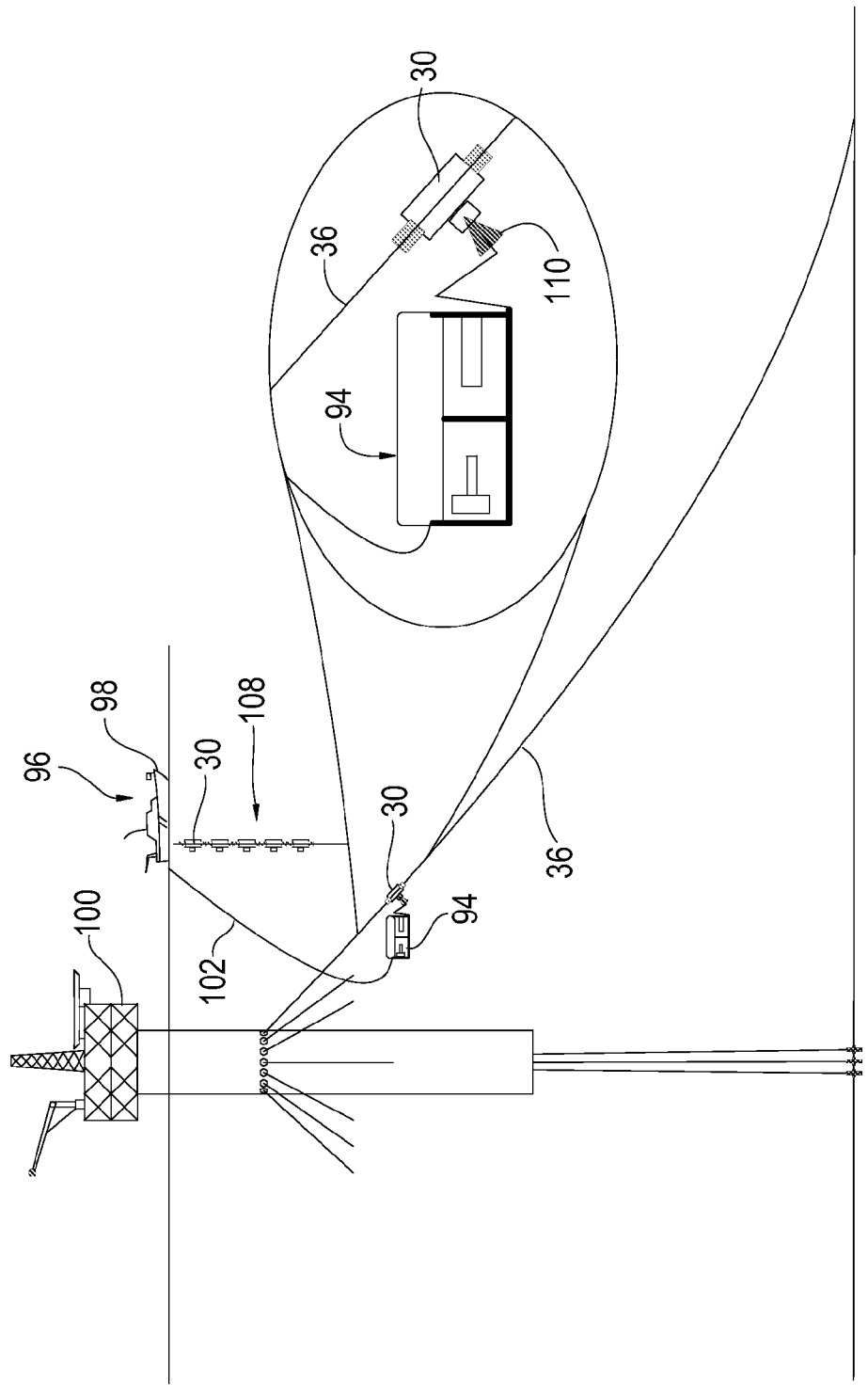
FIG. 13 is a perspective view of the ROV comprising a manipulator member placing the unmanned apparatus on the mooring line consistent with the embodiment illustrated in FIG. 12.

In one mode of untethered operation illustrated in FIGS. 12 and 13, an operator or ROV pilot, also aboard the vessel/structure 98,100, navigates the ROV 94 to a crawler 30 mounted on the deployment line 108 and detaches the crawler 30 from the deployment line with either the ROV's manipulator arm 110 or a purpose-built docking mechanism. The docking mechanism may be any mechanism known to one of ordinary skill in the art to allow for detachable attachment of the crawler to the ROV.

Typically, within approximately the first 100 feet of the surface, biological growth on the lines 36 precludes attachment of the crawler 30; therefore, the ROV pilot would use the ROV's 94 own cameras and sensors to perform the riser/mooring inspection. Immediately below the depth where most surface biological growth subsides, the ROV clamps the crawler vehicle onto the line employing the clamping mechanism 58 disclosed above. A linear actuator 71 or an operative force applied by the ROV to the grip bars 66 causes the hinged member 60 to separate the idler units 68,70 allowing for the elongated structure 36 or line to be disposed within the recess 34 of the crawler. Once the line contacts the drive unit 46 the operative force is removed from the grip bars by the ROV or the linear actuator is disengaged in order for the spring biased hinged member to allow for the idler units to engage the line. After the wheels 50 of the drive unit and idler units contact the line and the crawler is attached to the line, the ROV 94 may detach the crawler from the manipulator 110. The wheels are arranged in an axial ring with the wheels capable of rolling along the structure linked longitudinally in series or, in an alternate embodiment, tracks arranged in a similar fashion and surround the cable so as to maintain traction. The wheels assure positive locomotion via an active mechanical drive unit turning a chain linking the active drive wheels to an electrical turning actuator such as the Tecnadyne model 20WD rotary actuator along the line and keep the crawler from falling off of the mooring/riser.

Figure 14:
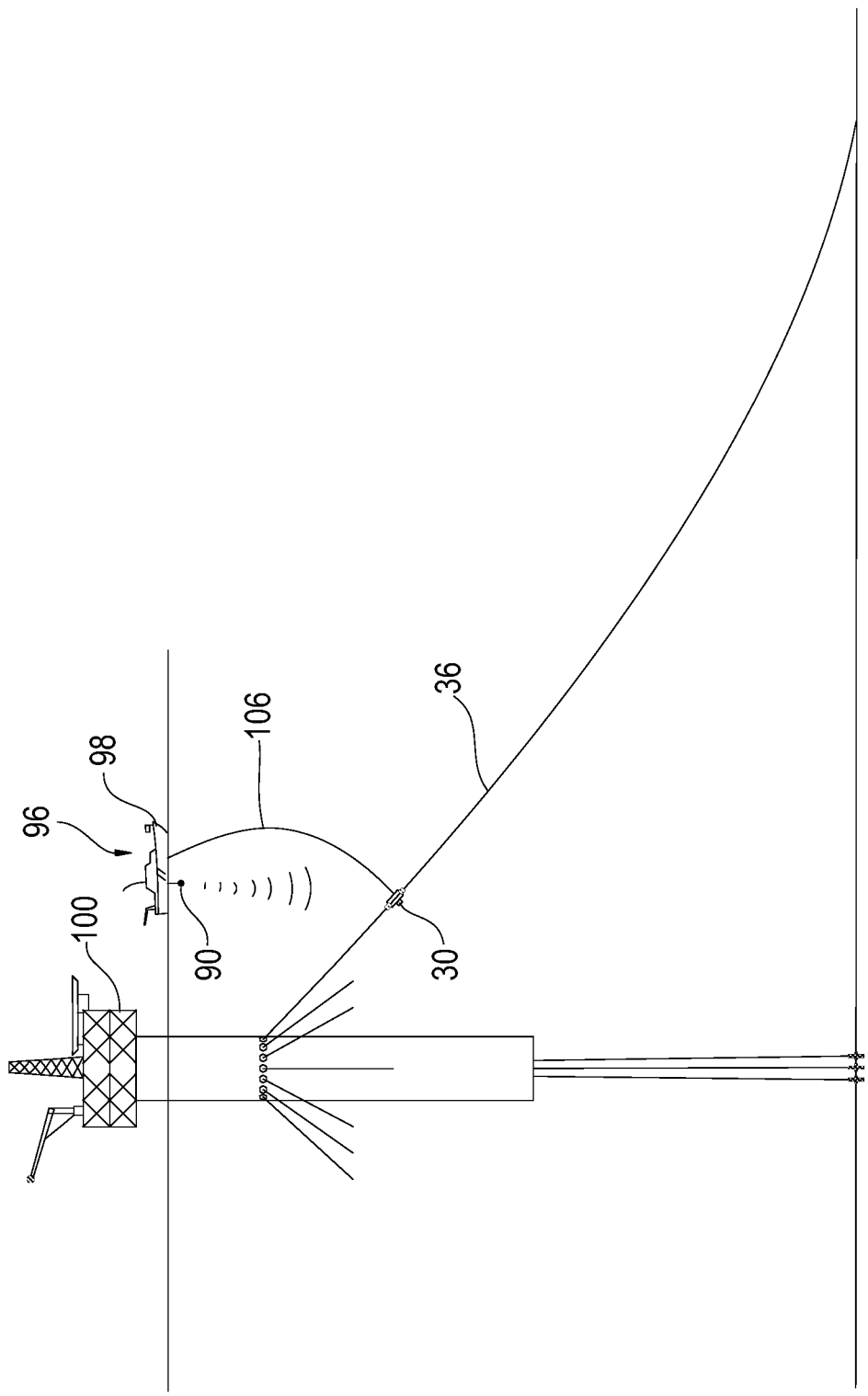
FIG. 14 is a perspective view of the unmanned apparatus attached to the mooring line while a transceiver/modem performs a diagnostics check on the unmanned apparatus consistent with the embodiment illustrated in FIG. 12. The launch assembly has been retracted out of the water.
Figure 15:
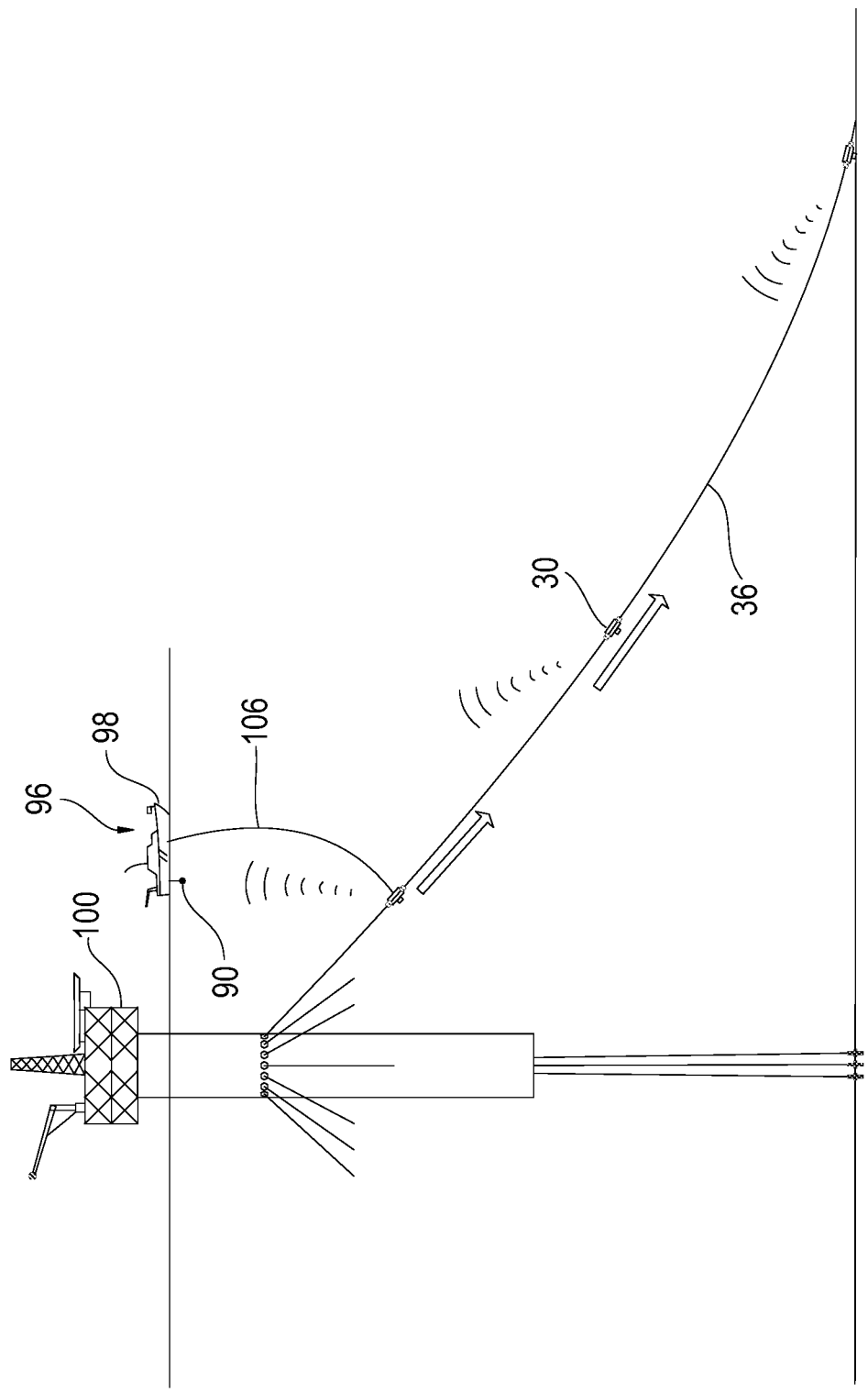
FIG. 15 is a perspective view of the unmanned apparatus attached to the mooring line while the transceiver/modem commands a clutch to disengage allowing the unmanned apparatus to freefall on the mooring line to the sea floor consistent with the embodiment illustrated in FIG. 12.

Typically, as illustrated in FIGS. 14 and 15, the crawler 30, which includes a clutch in at least one embodiment, stays in the attachment position with the clutch engaged until its operator commands it to descend. In one embodiment, once the crawler is established on the mooring or riser 36, the acoustic modem 90 awakens the vehicle for diagnostics. Upon successful diagnostics check, the crawler is commanded to release its clutch allowing the crawler to freefall to the bottom of the mooring or riser while being tracked from the surface via acoustic positioning. In one embodiment, upon acoustic command, the crawler disengages the clutch and freefalls or coasts down the line with the operator tracking its position acoustically via conventional acoustic positioning such as the Kongsberg Maritime 350P Ultrashort Baseline Acoustic Positioning System. Before acoustic tracking commences, a conventional CTD (Conductivity/Temperature/Depth) probe, such as the SBE 25 SEALOGGER CTD manufactured by Sea-bird Electronics, Inc. of Bellevue, Wash., is lowered through the water column to determine a sound velocity profile for the area of operation. Aboard the crawler is an acoustic transponder receiving a coded signal from a surface-mounted transceiver unit. The transponder responds to interrogation from the surface transceiver with a coded acoustic signal (via an underwater transducer) to the surface to resolve the slant-range distance between crawler and the surface transceiver. The bearing is resolved via time phase shift of the signal as it crosses the surface receiver transducer array. The combination of these range and bearing resolutions allow for accurate three-dimensional positioning subsea.

Figure 16:
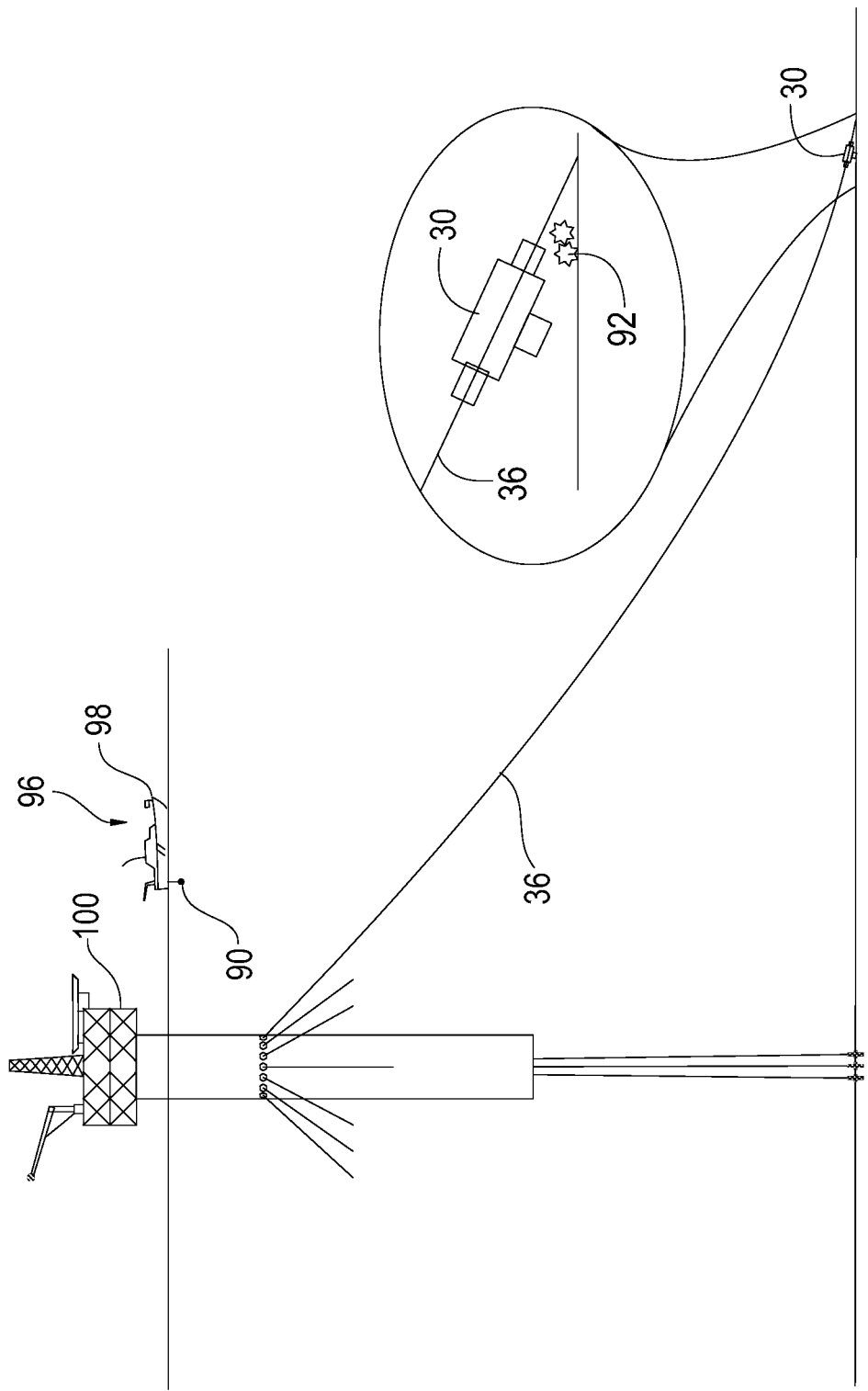
FIG. 16 is a perspective view of the unmanned apparatus attached to the line releasing a plurality of sacrificial weights to achieve positive buoyancy during ascent consistent with the embodiment illustrated in FIG. 12.
Figure 17:
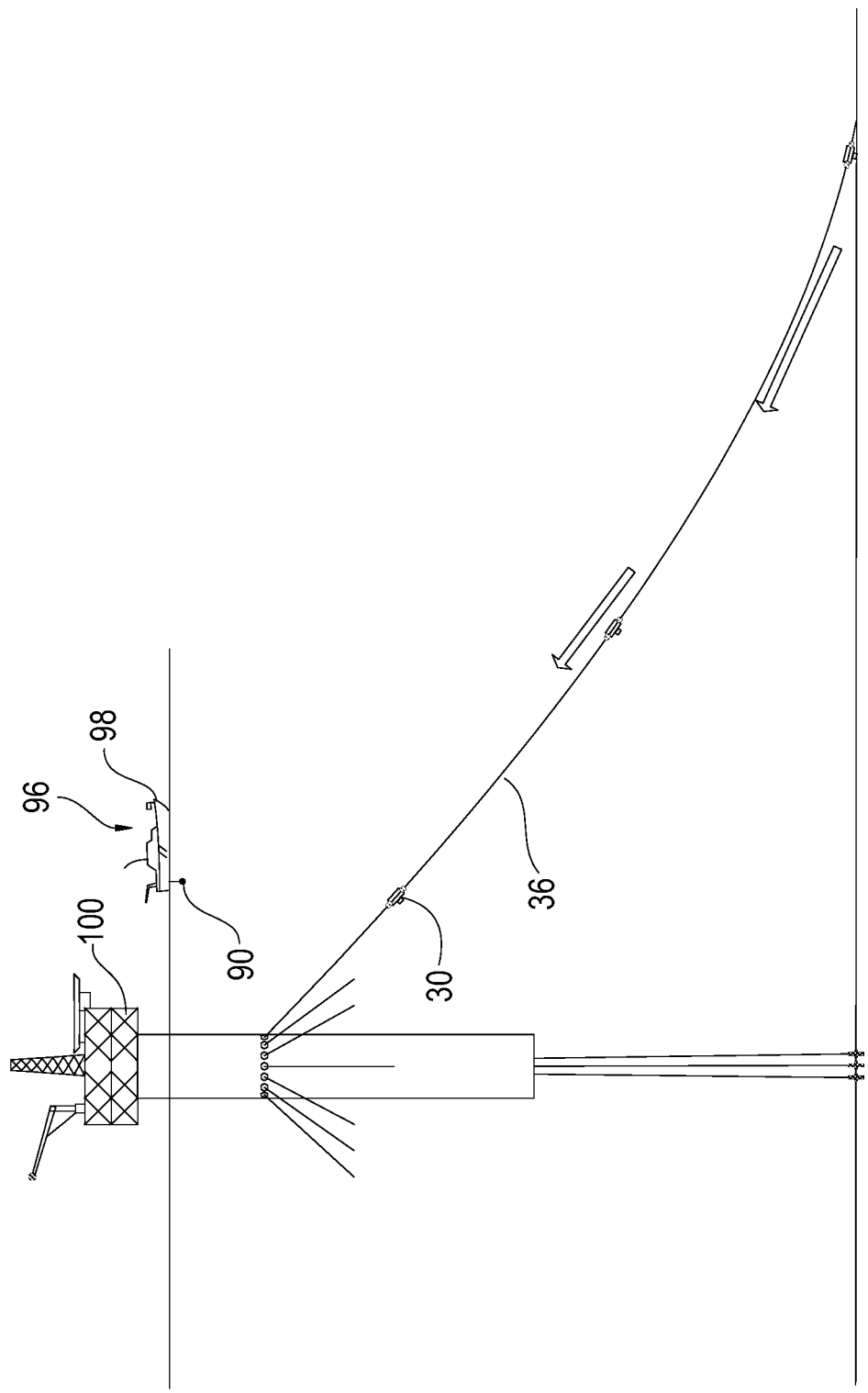
FIG. 17 is a perspective view of the unmanned apparatus attached to the mooring line whereby the clutch is engaged allowing the unmanned apparatus to ascend the mooring line at a constant speed performing an inspection of the mooring line consistent with the embodiment illustrated in FIG. 12 of the present invention.

After traversing as far as possible down the line 36, the operator may acoustically command the crawler 30 to drop the weight 92 as illustrated in FIG. 16, thus making the crawler slightly buoyant so as to increase climbing efficiency. The sacrificial ballast weight attached to the bottom of the crawler aids its descent and acts as a shock absorber upon bottom contact, should the crawler contact debris or the bottom. The secondary function of the high-speed travel down the line is for macro viewing of the line at higher speed as well as clearing the line of any light marine growth or debris before the detailed inspection commences upon ascent. In an alternate embodiment, a bump sensor may sense touchdown on the bottom of the seafloor, thus allowing the crawler to shed the sacrificial ballast weight so as to render the vehicle positively buoyant. The drive unit 46 is then engaged and the crawler 30 begins to crawl back up the line 36 towards the surface at a fixed rate allowing for even video and sensor coverage of the mooring/riser. The crawler's progress is acoustically tracked during inspection to note any discrepancies in movement as well as locating the crawler should it become snagged.

As mentioned above, the crawler may run either tethered or untethered. In the tethered configuration, a tertiary cable 106, illustrated as a coaxial cable in FIG. 14, would provide immediate video feedback to the surface control station 96. In the untethered configuration, the crawler would experience less drag, and multiple crawlers could crawl the structure(s) simultaneously with less chance of entanglement.

In one embodiment, on board the crawler, video from each of a ring of cameras surrounding the line is simultaneously recorded and time-stamped. In an alternate embodiment, the information is transmitted through the secondary or tertiary cable as the crawler runs back up the line. Additionally, data from any further on-board sensors such as a ultrasonic transducer, Radio Frequency (or Radiography—such as x-ray) electromagnetic radiation transmitter and eddy current detector(s) will be captured during the inspection transit of the line. During the ascent, the operator is able to monitor the crawler's position and status, and issue commands if necessary.

Figure 18:
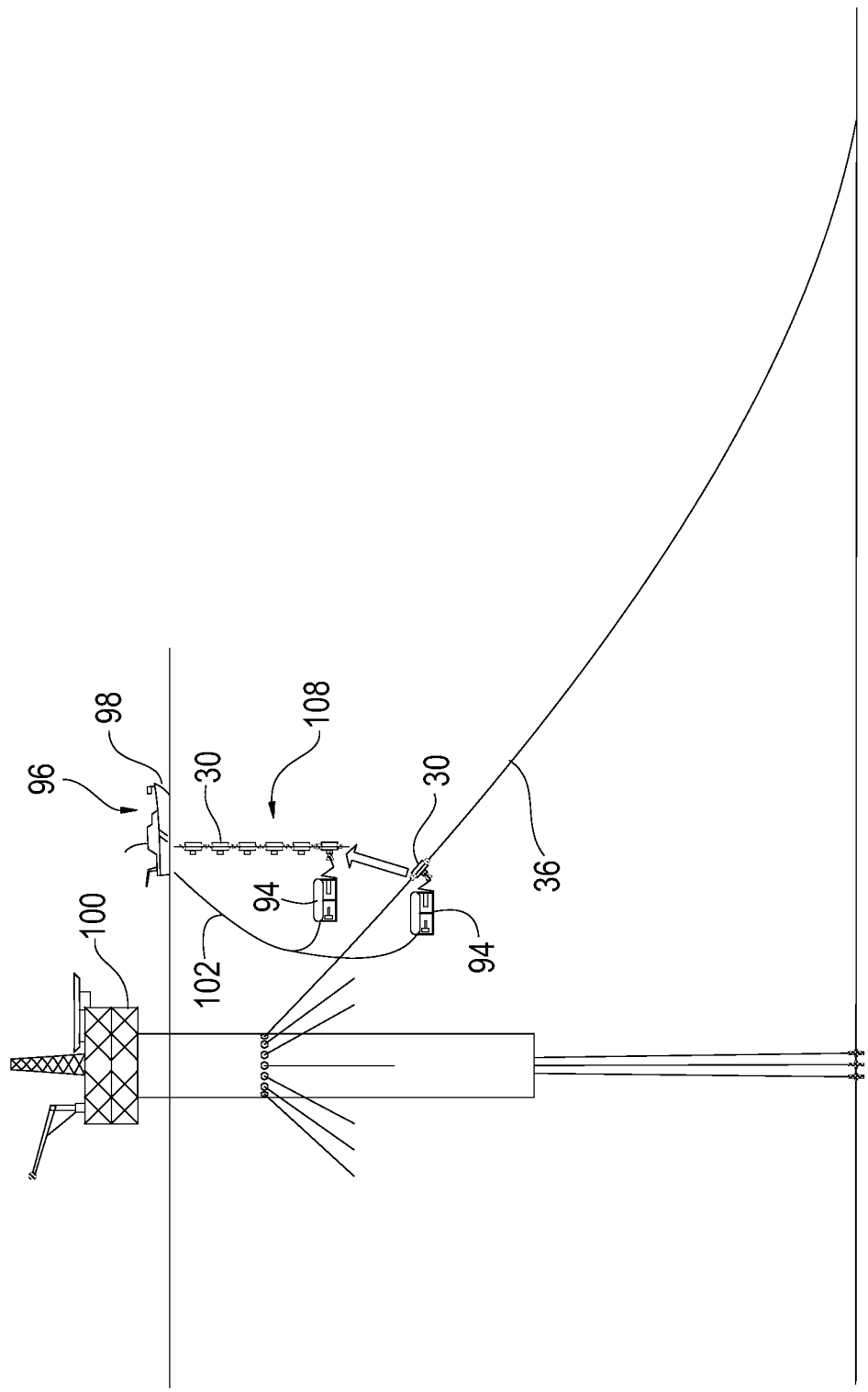
FIG. 18 is a perspective view of the ROV detaching the unmanned apparatus from the mooring line using the manipulator member and attaching the unmanned apparatus to the launch assembly consistent with the embodiment illustrated in FIG. 12.

As the crawler 30 returns to its starting depth as shown in FIG. 18, it automatically stops recording video/data and the drive unit 46 ceases and holds position. The ROV pilot then retrieves the crawler 30 from the line 36 and re-attaches it to the deployment/retrieval line 108. The crew of the vessel 98 may retrieve the deployment line from the water and remove the one or more crawlers from the deployment line. The crew may change recording media and batteries and perform other maintenance duties, as necessary. The process is then repeated for the other lines on the platform.

In an alternate embodiment, if the ROV drops the crawler vehicle from its manipulator before positively securing the crawler to the line, the operator may communicate acoustically with the crawler vehicle. The communications may include instructing the crawler to drop its ballast weights in order to assume a positive buoyancy for ease in retrieval. The retrieval would be aided by the use of the acoustic positioning beacon and strobe light for increased visibility. Once the crawler is retrieved by the ROV, it may be re-ballasted and reattached to the line.

In at least one embodiment, the crawler may become lodged on the elongated structure due to an obstruction on the line, the ROV may locate the crawler acoustically via an acoustic transponder as well as visually via the strobe light in order to move the crawler over the obstruction or to retrieve the vehicle to the surface.

In a scenario where the crawler malfunctions, the vehicle can either be retrieved by the ROV or the operator can acoustically instruct the vehicle to drop the sacrificial ballast. Once the ballast is dropped, the spring-loaded clamping mechanism may be released by command from the operator, thus allowing the crawler to float to the surface for visual retrieval. If the crawler completely loses power, the fail-safe mechanism on the clamping mechanism will default to an unclamped status thus detaching the crawler from the line and allowing it to float to the surface where it can be retrieved visually with use of its onboard strobe light.

In an alternate embodiment, the crawler operates in a tethered mode. Power, control and telemetry is derived real-time via the tether. The crawler 30 is coupled to a ROV 94 by a coupling member illustrated in FIGS. 19a and 19b as a connecting brace 114. In an alternate embodiment, the crawler is integral with the ROV. The coupled crawler and ROV travels to the elongated structure 36 or rope by the use of thrusters 118 mounted to the ROV and grasps the rope 36 by use of the crawler's clamping mechanism 58. Once the crawler is attached to the rope 36, command and locomotion is transferred to the crawler.

Once the crawler is clamped upon the rope by the clamping mechanism, it is attached so as to allow locomotion upon the line. In the tethered mode, the coupled ROV and crawler, upon encountering obstructions or non-compliant segments, may detach from the line then fly around the obstruction to then rejoin the line for continuation of the inspection.

Figure 20:
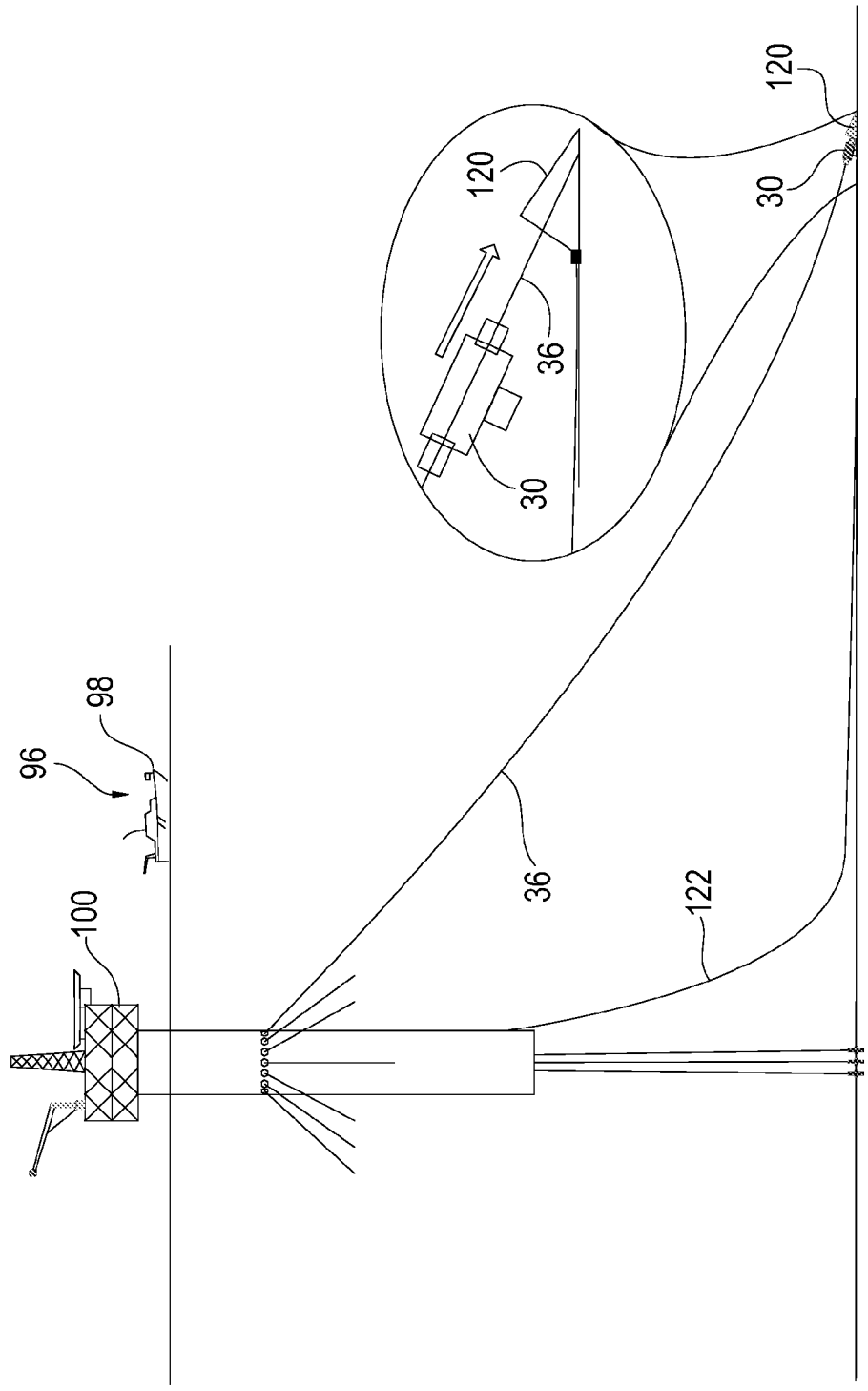
FIG. 20 is a perspective view of an unmanned apparatus attached to an elongated structure and docking with a docking station consistent with one embodiment of the present invention.
Figure 21:
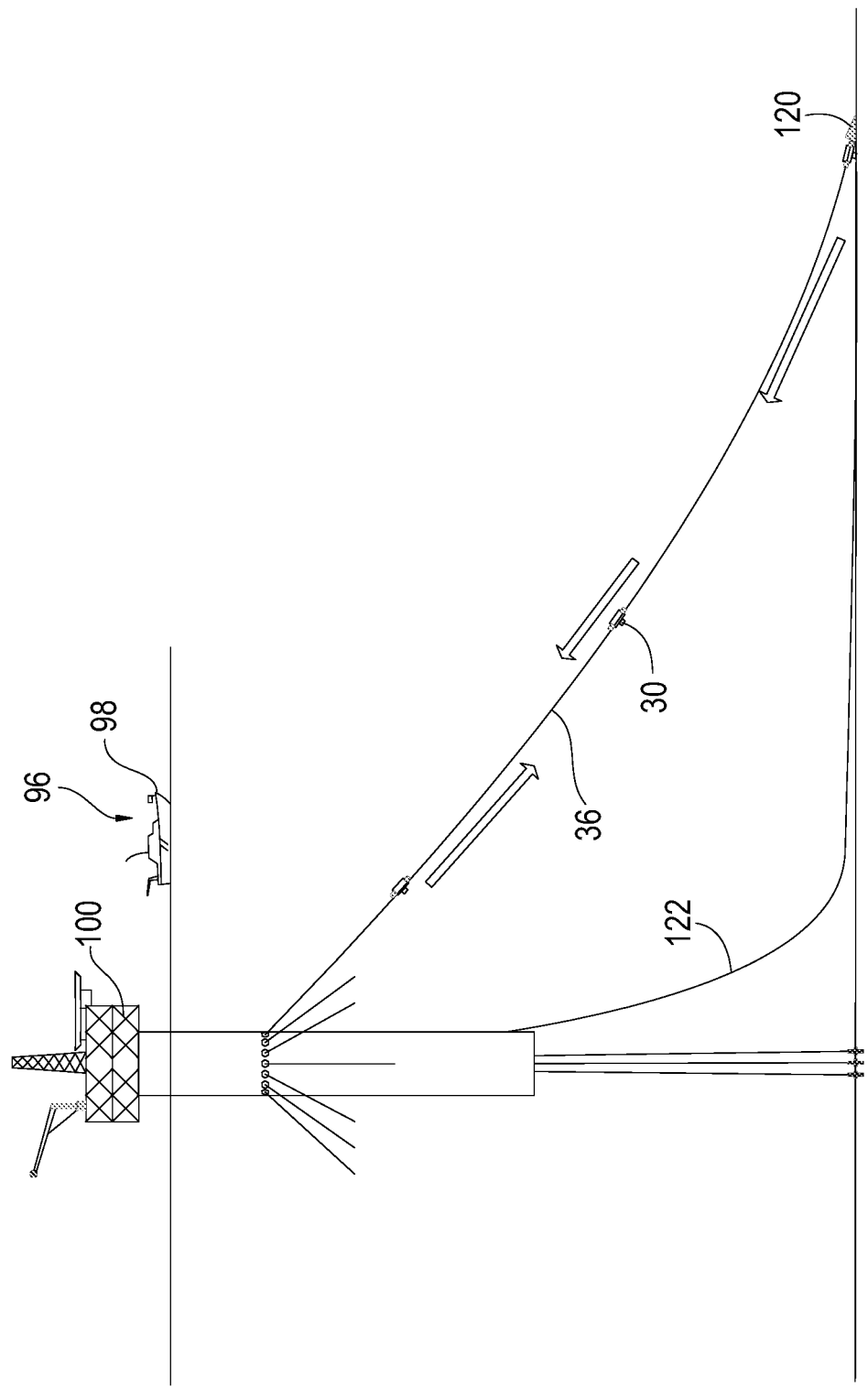
FIG. 21 is a perspective view of the unmanned apparatus attached to the elongated structure and inspecting and traversing the elongated structure after docking with the docking station consistent with the embodiment illustrated in FIG. 20.

In yet another mode of operation, illustrated in FIGS. 20 and 21, the crawler 30 may be a hybrid of tethered and untethered by detaching from a docking station 120 for recharging and data transfer and then driving the line 36 to then rejoin the docking station for data acquisition. The semi-autonomous crawler is similar in all respects to the untethered crawler except that the crawler is clamped semi-permanently to the line. The crawler is docked to a docking station where it exchanges data and instructions with the host platform as well as recharging its batteries. The crawler activates upon command then inspects the line in the normal fashion for a round trip back to the docking station for recharging and data exchange. The docking station may include a docking station cable 122 coupled to the surface control station or other power/data source including a surface relay station transmitting data/receiving instructions from a remote location with power received from a manned or unmanned surface or subsurface power station for recharging the energy storage device of the crawler. The docking station may also include wireless capabilities that allows for the transmission of information gathered from the crawler to be transmitted to the surface control station or location chosen by the operator of the surface control station.

In an alternate embodiment, the crawler may be used in terrestrial environments. Crawler may be attached to the elongated structure by use of an extending lifting device. The extending lifting device may be used to place the crawler on structures of varying height from the earth's surface. One such extended lifting device may be a crane or like lifting mechanism. In an alternate embodiment, the extended lifting device may be the human operator depending on the height of the structure to be inspected.

Except as may be expressly otherwise indicated, the article "a" or "an" if and as used herein is not intended to limit, and should not be construed as limiting, the description to a single element to which the article refers. Rather, the article "a" or "an" if and as used herein is intended to cover one or more such elements, unless the text expressly indicates otherwise.

Each and every patent or other publication or published document referred to in any portion of this specification is incorporated in toto into this disclosure by reference, as if fully set forth herein.

This invention is susceptible to considerable variation within the spirit and scope of the appended claims.

The invention claimed is:

1. An unmanned apparatus for use in traversing and inspecting at least a portion of an elongated structure, the unmanned apparatus comprising
at least one structural member defining a recess sized and configured to receive the portion of the elongated structure;
attachment means for attaching the unmanned apparatus to the elongated structure, the attachment means comprising traversal means for traversing at least the portion of the elongated structure, wherein the attachment means comprises a plurality of traction members operatively connected to the structural member and the traversal means comprises a locomotion system coupled to at least one of the traction members, and wherein the attachment means further comprises:
a first traction member coupled to the structural member, wherein the first traction member is proximate a top portion of the recess and the first traction member contacts the portion of the elongated structure when the portion of the elongated structure is disposed within the recess during use of the unmanned apparatus; and
a clamping mechanism comprising
(i) at least one hinged member coupled to the structural member,
(ii) a second traction member operatively coupled to the hinged member, and
(iii) a third traction member operatively coupled to the hinged member;
wherein the clamping mechanism is sized and configured so that the clamping mechanism may be selectively biased to contact or separate from the elongated structure and while the portion of the elongated structure is disposed within the recess and the clamping mechanism is biased to contact the elongated structure, the second traction member and the third traction member contact the elongated structure and, when the locomotion system is actuated while each traction member contacts the elongated structure, the unmanned apparatus traverses and inspects at least a portion of a length of the elongated structure; and
a plurality of cameras coupled to at least a portion of the unmanned apparatus, the cameras being configured so that the cameras are collectively capable of providing one or more images of the entire surface area of at least the portion of the elongated structure.

2. The unmanned apparatus of claim 1 wherein the first traction member, the second traction member, and the third traction member each comprises at least one wheel sized and configured for frictional contact with the portion of the elongated structure disposed in the recess.

3. The unmanned apparatus of claim 2 wherein the locomotion system comprises an electrical or hydraulic rotary actuator operatively coupled to at least one of the wheels.

4. The unmanned apparatus of claim 1 wherein the hinged member is operatively coupled to a linear actuator, wherein the linear actuator provides operative force to the hinged member.

5. The unmanned apparatus of claim 1 further comprising at least one of the following:
(i) at least one thruster coupled to the structural member or another portion of the unmanned apparatus, and
(ii) a housing coupled to the structural member.

6. The unmanned apparatus of claim 1 wherein the locomotion system is operatively coupled to the first traction member.

7. The unmanned apparatus of claim 1 wherein the first traction member, the second traction member, and the third traction member are substantially equidistant from each other when each of the first traction member, the second traction member, and the third traction member contact the portion of the elongated structure.

8. The unmanned apparatus of claim 1 further comprising at least one sensor coupled to at least one of the following:
(i) the structural member;
(ii) the first traction member;
(iii) the second traction member;
(iv) the third traction member;
(v) the housing;
(vi) the thruster; and/or
(vii) the locomotion system,
each sensor detecting at least one parameter indicative of the elongated structure, the external environment, and/or the unmanned apparatus.

9. The unmanned apparatus of claim 1 wherein the elongated structure is selected from the group consisting of a rope, a cable, an umbilical, a jacketed steel structure and a pipe.

10. A system to traverse and inspect at least a portion of an elongated underwater structure, the system comprising the unmanned apparatus of claim 1;
a remotely operated vehicle comprising at least one coupling member, the coupling member being sized and configured to couple the remotely operated vehicle to the unmanned apparatus;
a surface control station; and
a primary cable coupling the surface control station to the remotely operated vehicle, wherein the primary cable includes a coaxial cable or a twisted pair electrical conductor and/or an optical fiber, wherein the coaxial cable and twisted pair electrical conductor are capable of transmitting information and/or energy between the surface control station and the remotely operated vehicle and the optical fiber is capable of transmitting information between the surface control station and the remotely operated vehicle.

11. The underwater inspection and traversing system of claim 10 wherein the remotely operated vehicle further comprises at least one thruster.

12. The underwater inspection and traversing system of claim 10 wherein the elongated structure is selected from the group consisting of a rope, a cable, an umbilical, a jacketed steel structure and a pipe.

13. A system to traverse and inspect at least a portion of an elongated underwater structure, the system comprising
a surface control station located on a maritime vessel comprising a launch assembly, wherein a portion of the launch assembly is disposable in the water;
the unmanned apparatus of claim 1, the unmanned apparatus being sized and configured to detachably attach to the launch assembly;
a remotely operated vehicle comprising at least one manipulator member, the manipulator member sized and configured to detach the unmanned apparatus from the launch assembly and attach the unmanned apparatus to the elongated underwater structure; and
a primary cable coupling the surface control station to the remotely operated vehicle.

14. A method of traversing and inspecting at least a portion of an elongated structure using an unmanned apparatus, the method comprising
disposing a portion of the elongated structure within a recess defined by a structural member of the unmanned apparatus, the recess sized and configured to receive the portion of the elongated structure and the unmanned apparatus comprising
(i) attachment means for attaching the unmanned apparatus to the elongated structure when the elongated structure is disposed within the recess, the attachment means comprising traversal means for moving the unmanned apparatus relative to at least the portion of the elongated structure, wherein the attachment means comprises a plurality of traction members operatively connected to the structural member and the traversal means comprises a locomotion system coupled to at least one of the traction members, and wherein the attachment means further comprises
a first traction member coupled to the structural member, wherein the first traction member is proximate a top portion of the recess and the first traction member contacts the portion of the elongated structure when the portion of the elongated structure is disposed within the recess during use of the unmanned apparatus; and
a clamping mechanism comprising
(a) at least one hinged member coupled to the structural member,
(b) a second traction member operatively coupled to the hinged member, and
(c) a third traction member operatively coupled to the hinged member,
wherein, the clamping mechanism is sized and configured so that the clamping mechanism may be selectively biased to contact or separate from the elongated structure and while the portion of the elongated structure is disposed within the recess and the clamping mechanism is biased to contact the elongated structure, the second traction member and the third traction member contact the elongated structure and, when the locomotion system is actuated while each traction member contacts the elongated structure, the unmanned apparatus traverses and inspects at least a portion of a length of the elongated structure;
(ii) a plurality of cameras coupled to at least one portion of the unmanned apparatus, the cameras being configured so that the cameras are collectively capable of providing one or more images of the entire surface area of at least the portion of the elongated structure;
biasing at least a portion of the traversal means into contact with the portion of the elongated structure;
actuating the traversal means so that the unmanned apparatus traverses at least the portion of the elongated structure; and
capturing with the cameras one or more images of at least the portion of the elongated structure.

15. The method of claim 14 further comprising coupling the unmanned apparatus to a remotely operated vehicle, wherein the remotely operated vehicle comprises at least one thruster, the remotely operated vehicle positioning the unmanned apparatus so that the elongated structure is disposed within the recess.

16. The method of claim 15 further comprising transmitting energy and/or information between the remotely operated vehicle and a surface control station, the energy and/or information transmitted by a primary cable coupling the remotely operated vehicle to the surface control station.

17. The method of claim 15 further comprising transmitting energy and/or information between the remotely operated vehicle and the unmanned apparatus, the energy and/or information transmitted by a secondary cable coupling the remotely operated vehicle to the unmanned apparatus.

18. The method according to claim 15 further comprising disposing the unmanned apparatus on a launch assembly by an operator of a surface control station, the unmanned apparatus and launch assembly placed in the water and the remotely operated vehicle further comprises at least one manipulator member, the manipulator member sized and configured to couple and/or decouple the remotely operated vehicle to and/or from the unmanned apparatus.

19. The method according to claim 15 further comprising coupling at least one sensor to at least one of the following:
(i) the structural member;
(ii) the first traction member;
(iii) the second traction member;
(iv) the third traction member; and/or
(v) the locomotion system
of the unmanned apparatus, the sensor detecting at least one parameter indicative of the elongated structure, the external environment, and/or the unmanned apparatus.

20. The method according to claim 14 further comprising transporting the unmanned apparatus to the elongated structure by an extended lifting device.

21. A method of inspecting an elongated structure comprising
- traversing the elongated structure as in claim 14, wherein the elongated structure terminates proximate a docking station;
- coupling the unmanned apparatus to the docking station;
- transmitting energy and/or information between the docking station and the unmanned apparatus; and
- decoupling the unmanned apparatus from the docking station;
- traversing the elongate structure in a direction opposing the docking station; and
- inspecting the elongated structure as the unmanned apparatus traverses the elongated structure.

22. The method of claim 14 wherein the elongated structure is selected from the group consisting of a rope, a cable, an umbilical, a jacketed steel structure and a pipe.

23. An unmanned apparatus for use in traversing and inspecting at least a portion of an elongated structure, the unmanned apparatus comprising
- at least one structural member defining a recess sized and configured to receive the portion of the elongated structure;
- attachment means for attaching the unmanned apparatus to the elongated structure, the attachment means comprising traversal means for traversing at least the portion of the elongated structure, wherein the attachment means comprises a plurality of traction members operatively connected to the structural member and the traversal means comprises a locomotion system coupled to at least one of the traction members, and wherein the attachment means further comprises
- a first traction member coupled to the structural member, wherein the first traction member is proximate a top portion of the recess and the first traction member contacts the portion of the elongated structure when the portion of the elongated structure is disposed within the recess during use of the unmanned apparatus; and
- a clamping mechanism comprising
    (i) at least one hinged member coupled to the structural member,
    (ii) a second traction member operatively coupled to the hinged member, and
    (iii) a third traction member operatively coupled to the hinged member;
wherein the clamping mechanism is sized and configured so that the clamping mechanism may be selectively biased to contact or separate from the elongated structure and while the portion of the elongated structure is disposed within the recess and the clamping mechanism is biased to contact the elongated structure, the second traction member and the third traction member contact the elongated structure and, when the locomotion system is actuated while each traction member contacts the elongated structure, the unmanned apparatus traverses and inspects at least a portion of a length of the elongated structure; and
- at least one sensor coupled to a portion of the unmanned apparatus, the sensor comprising a transmitter proximate a receiver, wherein at least one wave form is transmitted from the transmitter to the elongated structure and thereafter received by the receiver, such that information regarding the elongated structure may be recovered from the wave form.

24. The unmanned apparatus of claim 23 wherein the elongated structure is selected from the group consisting of a rope, a cable, an umbilical, a jacketed steel structure and a pipe.

25. A system to traverse and inspect at least a portion of an elongated underwater structure, the system comprising
- the unmanned apparatus of claim 23;
- a remotely operated vehicle comprising at least one coupling member, the coupling member being sized and configured to couple the remotely operated vehicle to the unmanned apparatus;
- a surface control station; and
- a primary cable coupling the surface control station to the remotely operated vehicle.

26. A method of traversing and inspecting at least a portion of an elongated structure using an unmanned apparatus, the method comprising
- disposing a portion of the elongated structure within a recess defined by a structural member of the unmanned apparatus, the recess sized and configured to receive the portion of the elongated structure and the unmanned apparatus comprising
    (i) attachment means for attaching the unmanned apparatus to the elongated structure when the elongated structure is disposed within the recess, the attachment means comprising traversal means for moving the unmanned apparatus relative to at least the portion of the elongated structure, and
    (ii) at least one sensor comprising a transmitter proximate a receiver, wherein at least one wave form is transmitted from the transmitter to the elongated structure and thereafter received by the receiver, such that information regarding the internal portion of the elongated structure may be recovered from the wave form;
- biasing at least a portion of the traversal means into contact with the portion of the elongated structure;
- actuating the traversal means so that the unmanned apparatus traverses at least the portion of the elongated structure; and
- detecting with the sensor information regarding the internal portion of the elongated structure.

27. The method of claim 26 wherein the attachment means comprises a plurality of traction members operatively connected to the structural member and the traversal means comprises a locomotion system coupled to at least one of the traction members.

28. The method of claim 27 wherein the attachment means further comprises
- a first traction member coupled to the structural member, wherein the first traction member is proximate a top portion of the recess and the first traction member contacts the portion of the elongated structure when the portion of the elongated structure is disposed within the recess during use of the unmanned apparatus; and
- a clamping mechanism comprising
    (i) at least one hinged member coupled to the structural member,
    (ii) a second traction member operatively coupled to the hinged member, and
    (iii) a third traction member operatively coupled to the hinged member,
wherein, the clamping mechanism is sized and configured so that the clamping mechanism may be selectively biased to contact or separate from the elongated structure and while the portion of the elongated structure is disposed within the recess and the clamping mechanism is biased to contact the elongated structure, the second traction member and the third traction member contact the elongated structure and, when the locomotion system is actuated while each traction member contacts the elongated structure, the unmanned apparatus traverses and inspects at least a portion of a length of the elongated structure.

29. The method of claim 26 wherein the elongated structure is selected from the group consisting of a rope, a cable, an umbilical, a jacketed steel structure and a pipe.

* * * * *